US012702273B2

(12) United States Patent
Lord et al.

(10) Patent No.: US 12,702,273 B2
(45) Date of Patent: Aug. 11, 2026

(54) ENDOSCOPE WITH DISPOSABLE CAMERA SHAFT AND REUSEABLE HANDLE

(71) Applicant: PSIP2 LLC, Manchester, NH (US)

(72) Inventors: Bryan Lord, Bedford, NH (US); John M. Cronk, Strafford, NH (US)

(73) Assignee: PSIP2 LLC

(*) Notice: Subject to any disclaimer, the term of this patent is extended or adjusted under 35 U.S.C. 154(b) by 908 days.

(21) Appl. No.: 16/434,766

(22) Filed: Jun. 7, 2019

(65) Prior Publication Data

US 2019/0374095 A1 Dec. 12, 2019

Related U.S. Application Data

(60) Provisional application No. 62/850,326, filed on May 20, 2019, provisional application No. 62/722,150, (Continued)

(51) Int. Cl.
*A61B 1/00* (2006.01)
*A61B 1/05* (2006.01)
*A61B 1/06* (2006.01)

(52) U.S. Cl.
CPC ...... *A61B 1/00105* (2013.01); *A61B 1/00103* (2013.01); *A61B 1/053* (2013.01); (Continued)

(58) Field of Classification Search
CPC . A61B 1/053; A61B 1/00101; A61B 1/00103; A61B 1/00052; A61B 1/0676; (Continued)

(56) References Cited

U.S. PATENT DOCUMENTS 4,273,110 A 6/1981 Groux
4,765,313 A 8/1988 Kumakura
(Continued)

FOREIGN PATENT DOCUMENTS

CN 2551172 Y 5/2003
CN 2868212 Y 2/2007
(Continued)

OTHER PUBLICATIONS

PCT/IB2019/054783, International Search Report (Oct. 24, 2019).
(Continued)

*Primary Examiner* — Aaron B Fairchild
(74) *Attorney, Agent, or Firm* — Bond, Schoeneck & King, PLLC

(57) ABSTRACT

An endoscope with a handle and an insertion shaft. The insertion shaft has solid state illumination and imaging circuitry at or near a tip designed to provide illumination and imaging of the interior of a body cavity for a surgeon during surgery. The proximal portion of the handle has electronics for drive of the illumination circuitry and to receive imaging signal from the imaging circuitry, the proximal handle portion being designed to permit sterilization between uses. A joint between the proximal handle portion and the insertion shaft is designed to separably connect the insertion shaft to the proximal handle portion. When it is separated, the joint permits removal of the insertion shaft for disposal and replacement. The joint is designed so that, when connected, the joint can transfer mechanical force from a surgeon's hand to the insertion shaft, and provides electrical connectivity between the proximal handle circuitry and the illumination and imaging circuitry.

19 Claims, 22 Drawing Sheets

Related U.S. Application Data filed on Aug. 23, 2018, provisional application No. 62/682,585, filed on Jun. 8, 2018.

(52) U.S. Cl.
CPC ......... *A61B 1/00052* (2013.01); *A61B 1/0676* (2013.01); *A61B 1/0684* (2013.01)

(58) Field of Classification Search
CPC ... A61B 1/0684; A61B 1/126; A61B 1/00121; A61B 1/00105; A61B 1/00066; A61B 1/3132; A61B 1/00062; A61B 1/0052; A61B 1/015; A61B 1/123; A61L 2/10; A61L 2202/24
USPC .................................................. 600/136, 138
See application file for complete search history.

(56) References Cited

U.S. PATENT DOCUMENTS 4,852,551 A 8/1989 Opie
4,895,138 A 1/1990 Yabe
4,919,112 A 4/1990 Siegmund
4,964,710 A 10/1990 Leiner
4,997,084 A 3/1991 Opie
5,165,387 A 11/1992 Woodson
5,188,092 A 2/1993 White
5,377,047 A 12/1994 Broome
5,519,532 A 5/1996 Broome
5,573,493 A 11/1996 Sauer
5,653,677 A 8/1997 Okada
5,711,755 A 1/1998 Bonnell
5,718,664 A 2/1998 Peck
5,892,630 A 4/1999 Broome
6,293,910 B1 9/2001 Yamakita
6,605,260 B1 8/2003 Busted
6,652,452 B1 11/2003 Seifert
6,865,825 B2 3/2005 Bailey
7,033,317 B2 4/2006 Pruitt
7,239,805 B2 7/2007 Uyttendaele
7,413,543 B2 8/2008 Banik
7,427,262 B2 9/2008 Bonningue
7,479,106 B2 1/2009 Banik
7,530,946 B2 5/2009 Hartwick
7,976,559 B2 7/2011 Goldfarb
8,187,170 B2 5/2012 Naito
8,257,386 B2 9/2012 Lee
8,398,540 B2 3/2013 Hassidov
8,449,456 B2 * 5/2013 Ueno ................. A61B 1/00105 600/146
8,556,806 B2 10/2013 Farr
8,827,899 B2 9/2014 Farr
8,858,425 B2 10/2014 Farr
9,066,658 B2 6/2015 Hamel
9,107,574 B2 8/2015 Goldfarb
9,116,282 B2 8/2015 Kazakevich
9,242,069 B2 1/2016 Alt
9,271,637 B2 3/2016 Farr
9,364,249 B2 6/2016 Kimball
9,504,373 B2 11/2016 Vayser
9,877,654 B2 1/2018 Tesar
9,895,048 B2 2/2018 Ouyang
10,105,040 B2 10/2018 Ochi
10,278,563 B2 5/2019 Ouyang
10,780,187 B2 9/2020 Kang
11,141,045 B2 10/2021 Kucharski
11,185,216 B2 11/2021 Heni
11,278,194 B2 3/2022 Benning
11,357,593 B2 6/2022 Komp
2001/0031115 A1 10/2001 Chen
2004/0098040 A1 5/2004 Taniguchi
2005/0200707 A1 * 9/2005 Yogesan ............ A61B 1/00105 348/207.99
2005/0234294 A1 10/2005 Saadat et al.
2006/0149127 A1 7/2006 Seddiqui
2006/0276692 A1 12/2006 Kucklick
2007/0049794 A1 3/2007 Glassenberg et al.
2007/0162095 A1 * 7/2007 Kimmel ................. A61B 1/042 600/172
2007/0187626 A1 * 8/2007 Gaska ....................... A61L 2/10 250/504 R
2007/0202005 A1 * 8/2007 Maschke ................ G16H 40/40 422/62
2007/0225556 A1 9/2007 Ortiz
2007/0249904 A1 10/2007 Amano
2008/0027283 A1 1/2008 Matsui
2008/0051802 A1 2/2008 Schostek
2008/0195128 A1 * 8/2008 Orbay ................ A61B 1/00048 600/183
2008/0214896 A1 * 9/2008 Krupa ................ A61B 1/00105 600/141
2008/0287738 A1 * 11/2008 Adachi .............. A61B 1/00105 600/118
2008/0300456 A1 * 12/2008 Irion .................... A61B 1/0607 600/109
2009/0076329 A1 3/2009 Su
2009/0082630 A1 3/2009 Tulley
2010/0198009 A1 8/2010 Farr
2010/0204546 A1 8/2010 Hassidov
2011/0009694 A1 1/2011 Schultz et al.
2011/0028790 A1 2/2011 Farr
2011/0112361 A1 * 5/2011 Ishigami ............ A61B 1/00105 600/109
2011/0237880 A1 9/2011 Hamel
2012/0029280 A1 2/2012 Kucklick
2012/0116398 A1 5/2012 Goldfarb
2012/0197078 A1 8/2012 Stanley
2012/0310045 A1 * 12/2012 Hu ..................... A61B 1/00105 600/110
2013/0012783 A1 1/2013 Vayser
2013/0253499 A1 * 9/2013 Kimball ................. A61B 90/98 606/1
2014/0107416 A1 * 4/2014 Birnkrant ........... A61B 1/00124 600/110
2014/0114129 A1 4/2014 Peh
2014/0221749 A1 8/2014 Grant
2014/0243592 A1 8/2014 Kato et al.
2014/0275771 A1 9/2014 Henley
2015/0011830 A1 1/2015 Hunter
2015/0025311 A1 1/2015 Kadan
2015/0069728 A1 3/2015 Seitz, III
2015/0150441 A1 * 6/2015 Ouyang ................. A61B 1/015 600/109
2015/0164313 A1 * 6/2015 Ouyang ............. A61B 1/00105 600/103
2015/0173594 A1 6/2015 Farhadi
2015/0327886 A1 11/2015 Shen
2015/0374210 A1 12/2015 Durr
2016/0235286 A1 8/2016 Chiang
2017/0049298 A1 2/2017 Hunter et al.
2017/0070654 A1 3/2017 Ochi
2017/0078583 A1 * 3/2017 Haggerty ........... A61B 1/00071
2017/0182194 A1 6/2017 Shin
2017/0188795 A1 7/2017 Ouyang
2017/0245890 A1 8/2017 Ochi
2017/0252472 A1 * 9/2017 Dang ........................ A61L 2/16
2018/0084986 A1 3/2018 Ochi
2018/0168442 A1 6/2018 Schaeffer
2018/0235441 A1 * 8/2018 Huang ............... A61B 1/00142
2018/0296281 A1 10/2018 Yeung et al.
2018/0317762 A1 11/2018 Fowler et al.
2019/0038116 A1 2/2019 Ochi
2019/0298151 A1 10/2019 Frangioni
2019/0328217 A1 10/2019 Moreau
2019/0374095 A1 12/2019 Lord
2020/0000491 A1 1/2020 Washburn
2020/0222146 A1 7/2020 Komp
2020/0345218 A1 11/2020 Lord
2020/0397232 A1 12/2020 Ulmschneider
2021/0052145 A1 2/2021 Rauniyar
2021/0113068 A1 4/2021 Shin et al.
2021/0169316 A1 6/2021 Schultheis
2021/0330177 A1 10/2021 Kohno

(56) References Cited

U.S. PATENT DOCUMENTS

| | | | |
|---|---|---|---|
| 2022/0125280 | A1 | 4/2022 | Tyan |
| 2022/0378279 | A1 | 12/2022 | Poll |
| 2023/0123867 | A1 | 4/2023 | Herda et al. |

FOREIGN PATENT DOCUMENTS

| | | | | | |
|---|---|---|---|---|---|
| CN | 101040775 | | | 9/2007 | |
| CN | 101801278 | | | 8/2010 | |
| CN | 103315807 | | | 9/2013 | |
| CN | 107 157 429 | | | 9/2014 | |
| CN | 106308727 | | | 1/2017 | |
| CN | 106821285 | | | 6/2017 | |
| CN | 111458859 | A | | 7/2020 | |
| DE | 10330177 | A1 | | 3/2005 | |
| EP | 0904725 | B1 | | 9/2005 | |
| EP | 1 634 656 | A1 | | 3/2006 | |
| EP | 1902665 | A1 | | 3/2008 | |
| EP | 2266452 | | | 12/2010 | |
| EP | 4090270 | A1 | | 11/2022 | |
| JP | 2001-128923 | A | | 5/2001 | |
| JP | 2011-28923 | | | 5/2001 | |
| JP | 2002-512086 | | | 4/2002 | |
| JP | 2004-358107 | | | 12/2004 | |
| JP | 2007020797 | A | | 2/2007 | |
| JP | 4315489 | B2 | | 8/2009 | |
| JP | 2013192953 | A | * | 9/2013 | ............ A61B 90/90 |
| JP | 2014066923 | A | | 4/2014 | |
| KR | 20030073761 | A | | 9/2003 | |
| KR | 10-1614939 | | | 4/2016 | |
| KR | 20160044635 | A | | 4/2016 | |
| KR | 101784213 | B1 | * | 8/2017 | |
| KR | 20180041759 | A | | 4/2018 | |
| WO | WO1993/015648 | A2 | | 8/1993 | |
| WO | WO 2006/073676 | A1 | | 7/2006 | |
| WO | WO 2012/027581 | A2 | | 3/2012 | |
| WO | WO 2014/031192 | A1 | | 2/2014 | |
| WO | WO 2015/142720 | A1 | | 9/2015 | |
| WO | WO 2017/040692 | A1 | | 3/2017 | |
| WO | WO2017147605 | A1 | | 8/2017 | |
| WO | 2019234712 | A1 | | 12/2019 | |
| WO | WO 2021/161228 | | | 8/2021 | |
| WO | WO 2022/003569 | | | 1/2022 | |

OTHER PUBLICATIONS

PCT/IB2019/054783, Written Opinion of the International Searching Authority (Oct. 24, 2019).
European Patent Office, EP 19 746 152.8, Communication pursuant to Article 94(3) EPC (Sep. 28, 2021).
European Patent Office, EP 19746152.8, Applicant's reply to Communication pursuant to Article 94(3) (Feb. 7, 2022).
CN App. CN 201980038145.1 , Office Action with Search Report (Jun. 23, 2022).
CN App. CN 201980038145.1 , Office Action (Nov. 17, 2022).
EPO App. EP 19746152.8 , Extended European Search Report (Dec. 21, 2022).
EPO App. EP 19746152.8 , Communication pursuant to Article 94(3) EPC (Mar. 17, 2023).
PCT/IB2021/050359, ISA/210 International Search Report, and ISA/237 Written Opinion of the International Searching Authority (May 18, 2021).
PCT/IB2021/050359, Article 34 Amendment (excerpts) (Nov. 18, 2021).
PCT/IB2021/050359, International Preliminary Report on Patentabilty (Chapter II) (Mar. 4, 2022).
PCT/IB2022/058030, ISA/210 Search Report and ISA/237 Written Opinion of the International Searching Authority (Dec. 19, 2022).
PCT/IB2022/058030, Article 34 Amendment (Mar. 19, 2023).
PCT App. PCT/IB2022/054938, International Search Report and Written Opinion of the International Searching Authority (Nov. 29, 2022).
PCT/IB2021/055823, ISA/210 International Search Report and ISA/237 Written Opinion (Aug. 10, 2021).
PCT/IB2021/055823, Article 34 Amendment (Mar. 30, 2022).
PCT/IB2021/055823, Written Opinion (May 16, 2022).
PCT/IB2022/059262, ISA/210 International Search Report and ISA/237 Written Opinion of the International Searching Authority (Dec. 14, 2022).
Oksana Kehoe, Alison Cartwright, Ayman Askari, Alicia J El Haj, and Jim Middleton: Intra-articular injection of mesenchymal stem cells leads to reduced inflammation and cartilage damage in murine antigen-induced arthritis, Journal of Translational Medicine 12:157, doi:10.1186/1479-5876-12-157 (Jun. 3, 2014).
Benedetta Mazzanti, Bruno Lorenzi, Annalisa Borghini, Margherita Boieri, Lara Ballerini, Riccardo Saccardi, Elisabetta Weber, and Federica Pessina: Local injection of bone marrow progenitor cells for the treatment of anal sphincter injury: in-vitro expanded versus minimally-manipulated cells, Stem Cell Research & Therapy 7:85, doi 10.1186/s13287-016-0344-x (Jun. 21, 2016).
Steffi Sunny, George Cheng, Daniel Daniel, Peter Lo, Sebastian Ochoa, Caitlin Howell, Nicolas Vogel, Adnan Majid, Joanna Aizenberg, *Transparent antifouling material for improved operative field visibility in endoscopy*, Proceedings of the National Academy of Sciences U.S.A., Oct. 18, 2016;113(42):11676-11681. doi: 10.1073/pnas.1605272113 (Sep. 29, 2016).
Matthew J. Kraeutler, Tigran Garabekyan, Omer Mei-Dan, The use of platelet-rich plasma to augment conservative and surgical treatment of hip and pelvic disorders, Muscles, Ligaments and Tendons Journal 410 2016;6 (3):409-419 doi: 10.11138/mltj/2016.6.3.410 (Dec. 21, 2016).
Felix Asche, Basler AG, White Paper, Modern CMOS Sensors and Their Use in Fluorescence-Based Applications (Nov. 2017).
Eduardo Martín Arranz, María Dolores Martín Arranz, Tomás Robredo, Pablo Mancheño-Corvo, Ramón Menta, Francisco Javier Alves, Jose Manuel Suárez de Parga, Pedro Mora Sanz, Olga de la Rosa, Dirk Büscher, Eleuterio Lombardo, and Fernando de Miguel: Endoscopic submucosal injection of adipose-derived mesenchymal stem cells ameliorates TNBS-induced colitis in rats and prevents stenosis, Stem Cell Research & Therapy 9:95, doi: 10.1186/s13287-018-0837-x (Apr. 10, 2018).
René von Fintel, Basler AG, White Paper, Modern CMOS Cameras as Replacements for CCD Cameras (May 2018).
Raffy Mirzayan, Joseph D. Cooper, and Jorge Chahla, Carbon Dioxide Insufflation of the Knee in the Treatment of Full-Thickness Chondral Defects With Micronized Human Articular Cartilage, Arthroscopy Techniques, 7:10:e969-e973, doi: 10.1016/j.eats.2018.05.005 (Oct. 2018).
Martin J. Hoogduijn, Eleuterio Lombardo, Concise Review: Mesenchymal Stromal Cells Anno 2019: Dawn of the Therapeutic Era? Stem Cells Translational Medicine 00:1-9 doi: 10.1002/sctm.19-0073 (2019).
NanoSurgery Technology Corp., Product Technology, Introducing the NanoScope, http://nanosurgerytech.com/product-technology/ (accessed Sep. 15, 2019).
Trice Medical, Mi-eye 2 is the revolutionary alternative to a traditional MRI, https://tricemedical.com/mi-eye/ (accessed Jul. 25,. 2019).
Adaptive Surface Technologies, Inc., AST has brought two distinct product groups to market, https://adaptivesurface.tech (retrieved May 21, 2021.
Harvard University, Hansjörg Wyss Institute for Biologically Inspired Engineering at Harvard University, *TLP: A Non-Stick Coating for Medical Devices*, https://wyss.harvard.edu/technology/tlp-a-non-stick-coating-for-medical-devices (retrieved May 21, 2021).
CN App. CN 201980038145.1 , Reply to Office Action (Nov. 8, 2022).
Japan App. 2020-567600, Office Action issued Aug. 15, 2023.
Canada App. 3,102,585, Office Action (Oct. 6, 2023).
Canada App. 3,165,314, Office Action (Oct. 18, 2023).
EPO App. 19746152.8, Communication pursuant to Article 94 (Nov. 14, 2023).
EPO App. 21741290.7, Extended European Search Report (Dec. 18, 2023).

(56) References Cited

OTHER PUBLICATIONS

Indian Patent Application No. 202027054048, Hearing Notice (May 1, 2024).
PCT App. PCT/IB2022/058030, International Preliminary Report on Patentability (Dec. 24, 2023).
PCT App. PCT/IB2023/059287, International Search Report and Written Opinion (Dec. 28, 2023).
Japan App. 2020-567600, Office Action (Nov. 28, 2023).
Japan App. 2020-567600, Office Action (Mar. 7, 2023).

* cited by examiner

ENDOSCOPE WITH DISPOSABLE CAMERA SHAFT AND REUSEABLE HANDLE

This application is a nonprovisional of U.S. Provisional applications 62/850,326 filed May 20, 2019, 62/722,150 filed Aug. 23, 2018 and 62/682,585 filed Jun. 8, 2018, each titled "Endoscope with Disposable Camera Shaft," all of which are incorporated by reference.

BACKGROUND

This application relates to endoscopes, laparoscopes, arthroscopes, colonoscopes, and similar apparatus, instruments, implements, or processes specially adapted or intended to be used for evaluating, examining, measuring, monitoring, studying, or testing living or dead human and animal bodies for medical purposes.

SUMMARY

In general, in a first aspect, the invention features an endoscope. The endoscope has a handle and an insertion shaft. The insertion shaft has solid state illumination and imaging circuitry at or near a tip designed to provide illumination and imaging of the interior of a body cavity for a surgeon during surgery. The proximal portion of the handle has electronics for drive of the illumination circuitry and to receive imaging signal from the imaging circuitry, the proximal handle portion being designed to permit sterilization between uses. A joint between the proximal handle portion and the insertion shaft is designed to separably connect the insertion shaft to the proximal handle portion. When it is separated, the joint permits removal of the insertion shaft for disposal and replacement. The joint is designed so that, when connected, the joint can transfer mechanical force from a surgeon's hand to the insertion shaft, and provides electrical connectivity between the proximal handle circuitry and the illumination and imaging circuitry.

In general, in a second aspect, the invention features a method for performance with an endoscope having a handle and an insertion shaft, the insertion shaft having solid state illumination and imaging circuitry at or near a tip designed to provide illumination and imaging of the interior of a body cavity for a surgeon during surgery, and the proximal portion of the handle having electronics for drive of the illumination circuitry and to receive imaging signal from the imaging circuitry, the proximal handle portion being designed to permit sterilization between uses; and a joint between the proximal handle portion and the insertion shaft designed to separably connect the insertion shaft to the proximal handle portion. The joint is separated to permit removal of the insertion shaft for disposal and replacement. The joint is reconnected with a new insertion shaft, the connection designed to provide mechanical force transfer between a surgeon's hand to the insertion shaft, and electrical connectivity between the proximal handle circuitry and the illumination and imaging circuitry.

Embodiments of the invention may include one or more of the following features. The handle may have proximal and distal portions. The distal portion may lie between the insertion shaft and proximal handle portion. The insertion shaft may be rigidly affixed to the distal handle portion. The joint may be disposed to connect and disconnect the distal and proximal portions of the handle. The distal handle portion may be designed to indirectly transfer mechanical force between a surgeon's hand to the insertion shaft, and provide indirect electrical connectivity between the proximal handle circuitry and the illumination and imaging circuitry. The handle may have a rotation collar having surface features designed to assist the surgeon in rotating the insertion shaft in the roll dimension about the axis of the insertion shaft relative to the proximal handle portion. The electronics inside the proximal handle portion may be designed to sense roll of the insertion shaft, and provide an angular rotation signal designed to permit righting of a displayed image received from the imaging circuitry. A mounting for the image sensor may be designed to permit panning of the image sensor about a pitch or yaw axis perpendicular to the central axis of the insertion shaft. One or more ultraviolet LEDs internal to the endoscope may be designed to sterilize a region of the interior of the endoscope. Hoses for insufflation fluid or gas may be designed on lie on or near a central axis of proximal handle portion. Two or more insertion shafts each having dimensions different than the others, may each be connectable to the proximal handle portion at the joint, to permit use of the proximal handle in surgery with different requirements for insertion shaft. A sterilization cabinet may be designed to sterilize components of the endoscope.

The above advantages and features are of representative embodiments only, and are presented only to assist in understanding the invention. It should be understood that they are not to be considered limitations on the invention as defined by the claims. Additional features and advantages of embodiments of the invention will become apparent in the following description, from the drawings, and from the claims.

DESCRIPTION

I. Overview

Figure 1A:
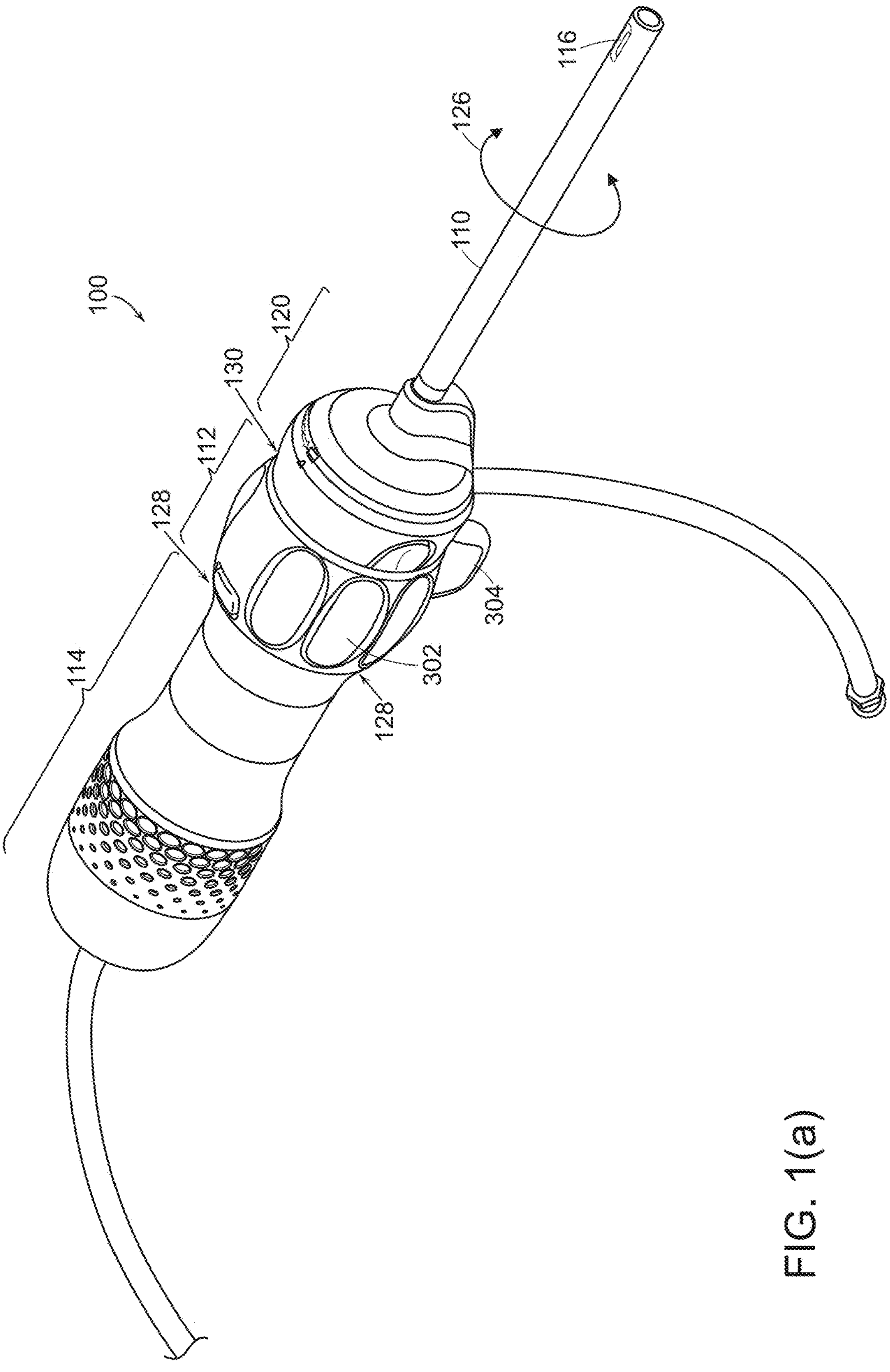
FIGS. 1(*a*), 1(*b*), 1(*c*), 1(*d*), 2(*d*), 3(*a*), 3(*e*), 3(*g*), 4(*a*), and 5(*a*), 5(*b*), and 5(*d*) are perspective views of endoscopes.
Figure 1B:
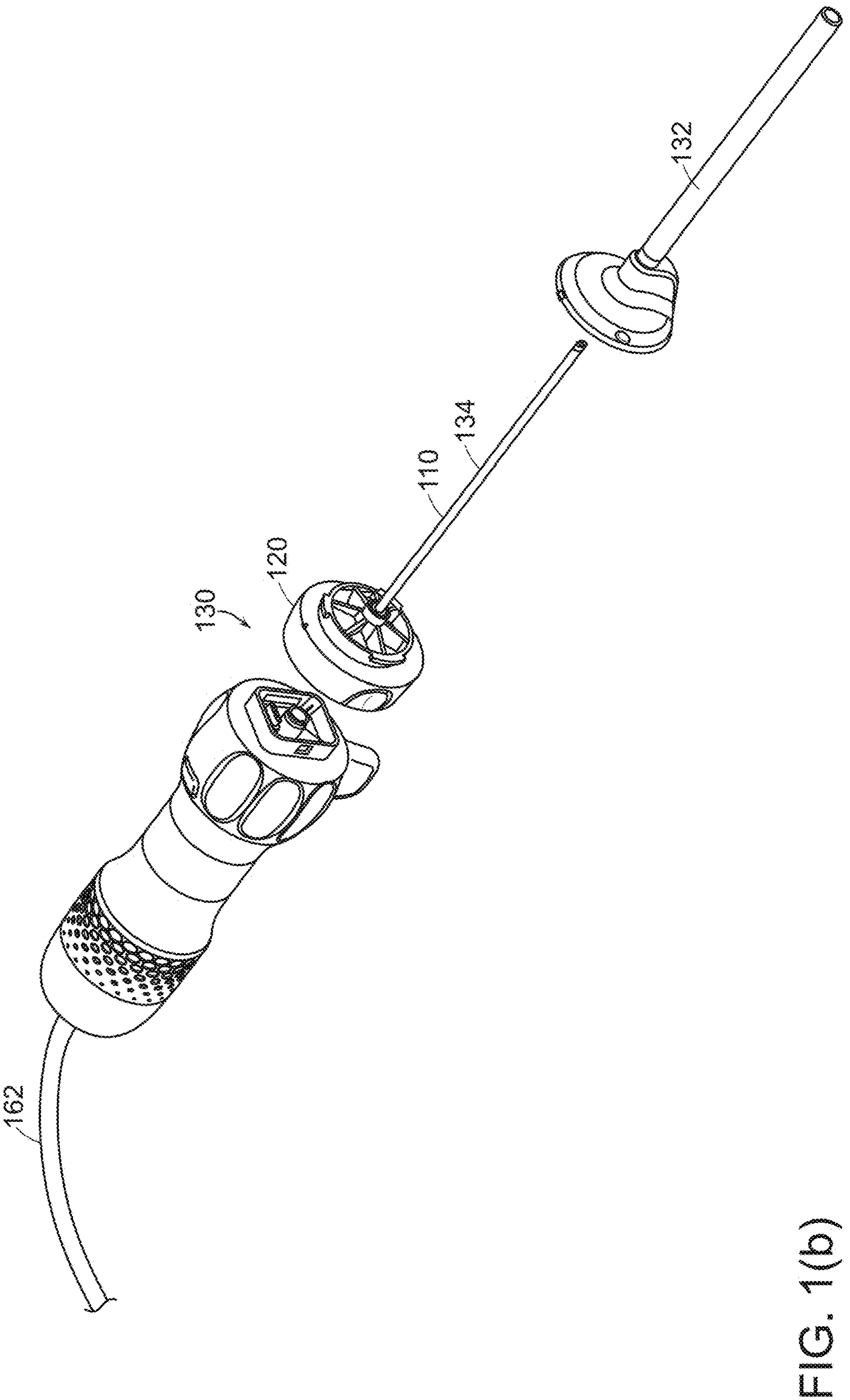
Figure 1C:
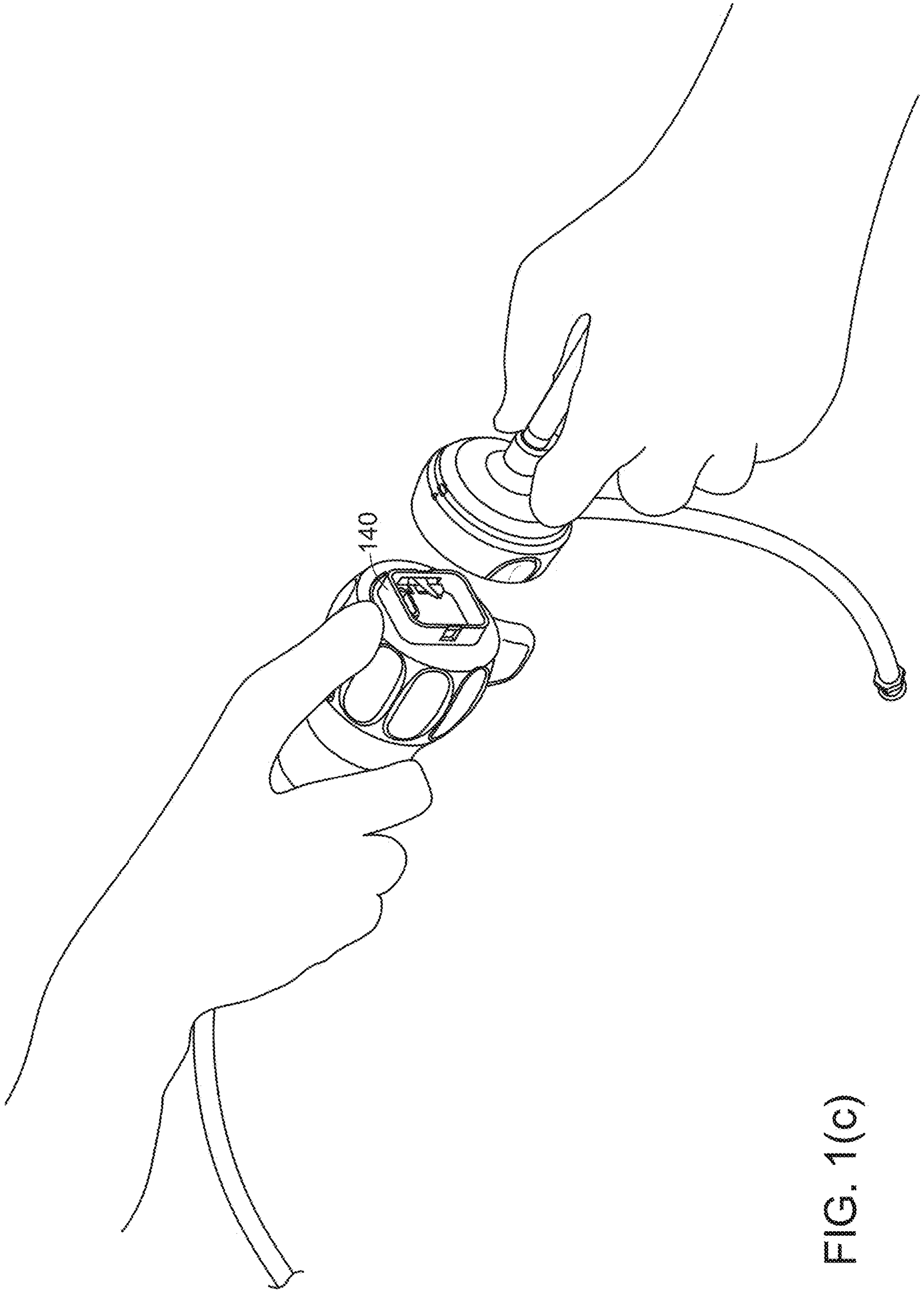
Figure 1D:
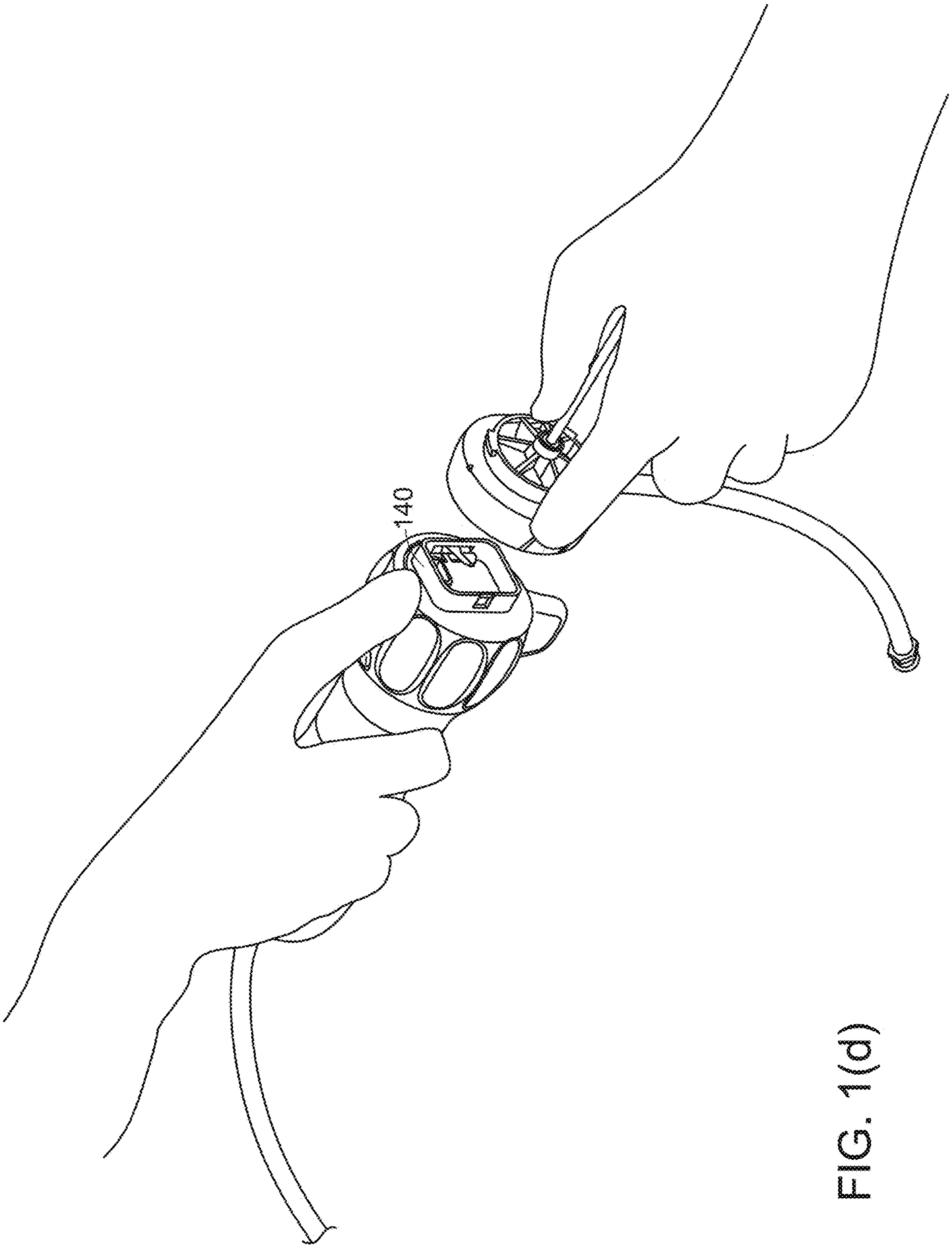

Referring to FIGS. 1(*a*), 1(*b*), 1(*c*), and 1(*d*), a surgical endoscope 100 may be structured to permit detachment of a shaft 110 portion from the endoscope's handle 112, 114. A camera or image sensor at tip 116 of the shaft, any panning mechanism, illumination, power and signal connectors, and fluid flow channels may be in the disposable shaft 110. Handle 112, 114 may be designed to be reusable (which implies that handle 112, 114 may be sterilizable, for example in an autoclave or other sterilization device, or protectable by a disposable sterility sleeve). Joint 130 between the detachable shaft and the reusable parts of handle 112, 114 may be generally distal in the handle (but not necessarily at the distal-most end). The replaceable shaft portion 110 may be disposable, along with a disposable portion 120 of the handle that is disposable with shaft 110.

II. Reposability: Partially Reusable, Partially Disposable/Replaceable, and a Coupling Joint Between Referring to FIGS. 1(*a*), 1(*c*), 2(*a*), 2(*b*), 2(*c*), 2(*d*), and 3(*a*), the handle of the endoscope 100 may include three principle components:

- The disposable cap 120. This distal-most portion of the handle may serve as a mounting base for shaft 110, and may disconnect from the remainder 112, 114 of the handle. This disposable cap portion 120 (along with shaft 110 and componentry inside) may be disposable.
- Rotation collar 112 may have surface features 302, 304 to allow a surgeon to rotate the rotation collar 120 about the central axis of the handle, that is, about the roll axis 126 of the shaft. During surgery, insertion shaft 110, disposable cap 120 and rotation collar 112 may be locked to rotate with each other, so that rotating the rotation collar effects rotation 126 of the disposable cap 120 and shaft 110.
- Proximal stationary handle 114 has a shell surrounding componentry within the handle. The outer diameter and outer surface of handle 114 may be designed to provide an easy and low-slip grip for a surgeon's hand. Joint 128 between the proximal handle and rotation collar may allow these two components to rotate relative to each other. In some cases, a circuit board and similar componentry inside proximal handle 114 may rotate with disposable cap 120 and rotation collar 112, inside proximal handle 114.

Disposable cap 120 and rotation collar 112 may be separable from each other at joint 130, so that disposable cap 120 and shaft 110 may be disposable, while handle 114 and rotation collar 112 (and componentry inside them) are reusable.

Referring to FIGS. 1(*a*), 1(*c*), 1(*d*), and 3(*a*), between the disposable cap 120 and rotation collar 112, three basic connections may be made:

- A rotation-locking coupling 140, 142 to hold the disposable portion 120 to the reusable handle 112, 114. Coupling 140, 142 may have sufficient strength to transmit insertion and withdrawal forces, roll, pitch, and yaw torques, lateral forces, and similar forces from the proximal reusable handle 112, 114 to the distal disposable portion 120 and shaft 100, thereby to allow a physician to aim the illumination and/or camera as needed. Joint 130 between disposable cap 120 and rotation collar 112 may lie generally toward the distal end of the handle. The disposable cap and rotation collar 112 may engage through flat force-transmittal surfaces 144 at the center of joint 130 and around the circumferences, so that these forces are supported around the circumference of separable joint 130. One or more release buttons 146 may be pressed or squeezed to cause one or more locking snaps 148 to disengage. The mechanical connection may include a rotatable locking ring or other release/fixation mechanisms.
- An electrical connection to supply power to the illumination source and camera, and to carry optical signals back from the camera to the processing board in handle 112, 114 and display system outside the endoscope. The disconnectable electrical connections for power and signal may be effected by a USB-C connector 150, 152, mini HDMI connector, or similar connector that can maintain signal integrity for high speed signals. If illumination is conveyed by optical fiber, joint 130 may include an optical connector.
- A disconnectable connection to any panning mechanism for the camera may be effected by a physical connector, such as a linkage.

In some cases, the camera/image sensor, LED, and electronic connections (and any mechanical connections for panning the camera/image sensor) may be removable from insertion shaft 110. Shaft 110 and cap 120 may be smooth and simple enough in shape to allow easy sterilization. Similarly, once the electronics are removed from interior of shaft 110, they may be sterilizable as well. it may be cost-effective, especially in lower-labor-cost markets, to disassemble, sterilize, and reassemble the shaft and its interior components for reuse.

One or more fluid hoses 160 for irrigation liquid or inflation gas (or two hoses, one for fluid and one for gas) may enter through disposable cap 120, so that the entire set of fluid tubing for the irrigation/inflation channel may be disposable with the disposable shaft portion. In other cases (e.g., FIGS. 5(*a*) and 5(*b*)), a fluid hose 162 may enter the proximal end of the scope, and disconnectable fluid connections within joint 130 for fluid inflow and outflow may be effected by gaskets, O rings, and the like. Alternatively, connectors for the hoses may be outboard of the endoscope itself, either near the endoscope (for applications where it may be desirable to allow "quick change" replacement of the insertion shaft in the course of a single procedure), or far from the endoscope, typically at the receptacle for waste fluid, to ease disposal of all hoses that are potentially contaminated by contact with the patient.

Disposable shaft 110, 120 may be designed to facilitate disposability of components that come into contact with bodily fluids. Because sterilization is often imperfect, patient safety may be improved by disposing of components that have come into contact with patient bodily fluids. To improve sterilizability, it may desirable to reduce componentry in the disposable component 110, 120 so that cost of the disposable component may be reduced, and to reduce surface features and crevices that may be difficult to sterilize. Thus, the lens, image sensor, LED, panning mechanism, and shaft may be disposable. In addition, because shaft 110 is used for fluid inflow and outflow, and is disposable, sealing against bodily fluids may be unnecessary.

Referring to FIG. 5(*c*), hoses 160, 162 for irrigation/insufflation fluid/gas in, irrigation/insufflation fluid/gas out, and electrical connection cord 164 may be permanently affixed 540, 542 to disposable cap 120. This arrangement may allow that hose 162 that carries water out of the surgical cavity, and which is therefore contaminated, may be disposable, and no fluid will come into contact with the reusable part 114 of the handle. Hoses and cord 160, 162 may be routed through channel 554 running the length of reusable handle 112, 114. Channel 544 may be of inner diameter large enough to permit easy passage of hoses and cord 160, 162, 164, and connectors 550, 552, and have a continuous smooth wall that permits easy sterilization, to permit ready replacement of the replaceable components. Channel 554 may be off the central axis, to allow printed circuit board 422 to lie on the central axis. Connectors 550, 552 at the end of hoses and cords 160, 162 may be small enough to pass through channel 554. Thus, replacement of shaft 110, cap 120, hoses and cords 160, 162 may be effected by threading connectors 550, 552 and hoses and cord 160, 162 through channel 544. Electrical cord 164 may have a connector 554 at or near joint 130, and hose(s) 160 for irrigation/insufflation fluid/gas flowing into the surgical cavity may likewise have a connector at joint 130 to allow this hose(s) to be reusable, or may be permanently affixed 540 to reduce possibility of leaking. Having hoses and cable 160, 162 roughly on-axis reduces undesirable cable flop as the scope is in use, and reduces undesirable torque on cap 120. Forming shaft 120, cap 120, and hoses 160, 162 as an integral unit for replacement reduces possibility of leaking, and improves sterility of the replacement operation.

Referring to FIG. 5(*d*), the replaceable/disposable shaft and its mounting componentry may be specialized to different types of surgery. For example, a replaceable disposable cap/shaft unit 110, 120 for laparoscopic thoracic surgery may have a shaft of 400 mm length and diameter of 10 mm. Replaceable components for arthroscopic surgery of knees and hips may be 155 mm in length, and 5.5 mm or 4 mm in diameter. For small joints, a replaceable shaft of 2.9 mm diameter or less may be preferred. Typical dimensions for various surgical specialties may be as follows (measured in millimeters):

| | | Cannula diameter | | Scope diameter | |
|---|---|---|---|---|---|
| Scope Type | Discipline | Min | Max | Min | Max |
| Arthroscope (small joint) | Arthroscopy | 2.8 | 4.0 | 1.9 | 2.9 |
| Arthroscope (large joint) | Arthroscopy | 4.7 | 6.0 | 2.9 | 5.3 |
| Cytoscope | Cytoscopy | | | 2.9 | 5.3 |
| Encephaloscope | ENT | | | 2.0 | 4.0 |
| Hysteroscope | Gynecology | 3.7 | 7.0 | 2.0 | 5.0 |
| Laparoscope | Laparoscopy | | | 2.0 | 10.0 |
| Sinuscope | ENT | | | 2.0 | 4.0 |
| Thoracoscope | Pulmonary | | | | 10 |

Various replaceable components 110 may have different instruments at tip 116. For example, various replaceable shafts may have cameras oriented at 0° (directly on-axis), 30°, 45°, 70°, and 90°.

Referring to FIG. 1(*b*), disposable shaft portion 110, 120 may in turn be separable into an outer cannula 132 for protection and strength, and an inner shaft portion 134 carrying various illumination, optical, and fluid-carrying componentry.

III. Additional Features of an Endoscope

Figures 2A, 2B, 2C:
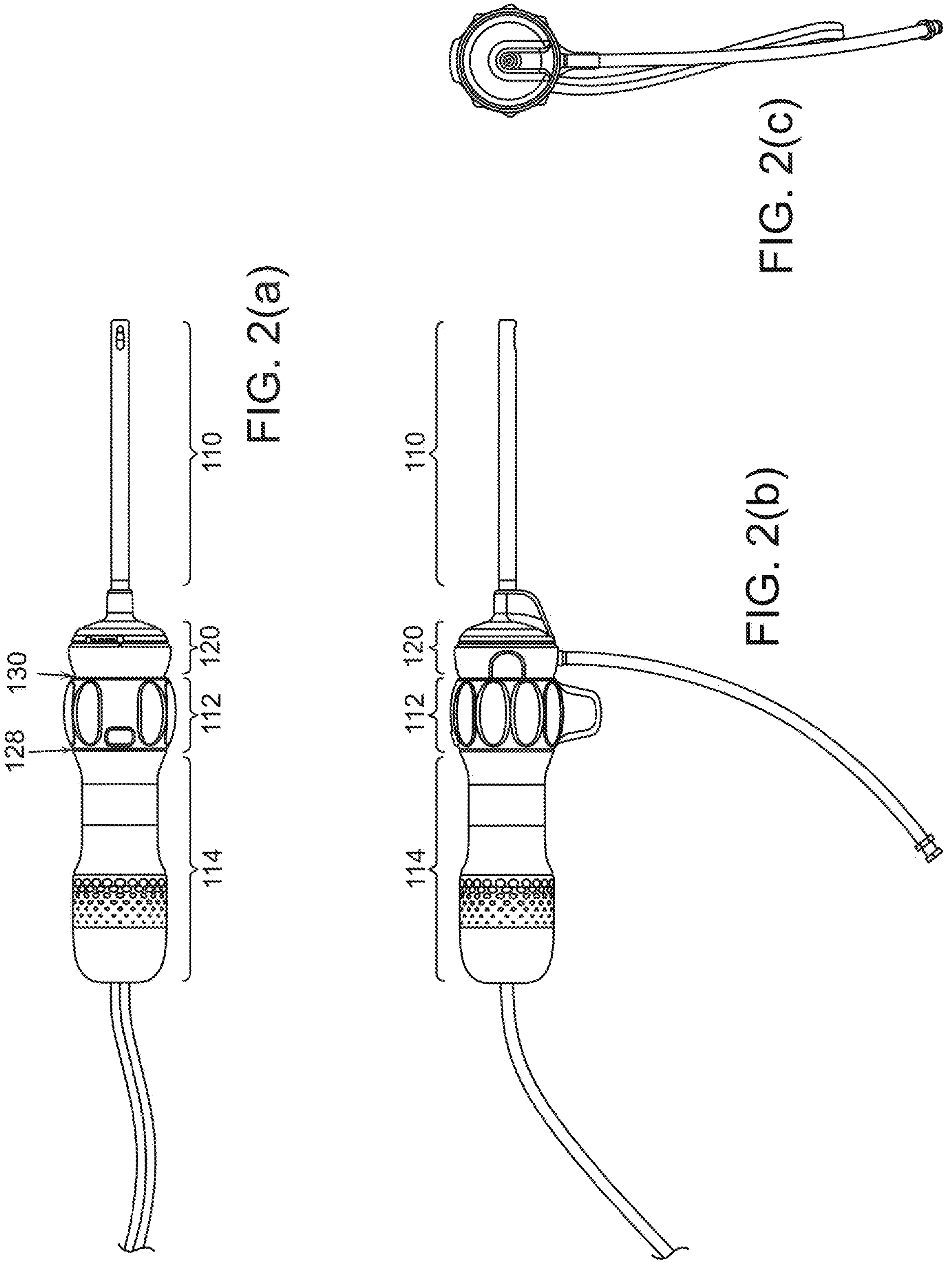
FIGS. 2(*a*), 2(*b*), and 2(*c*) are plan views of endoscopes.
Figure 2D:
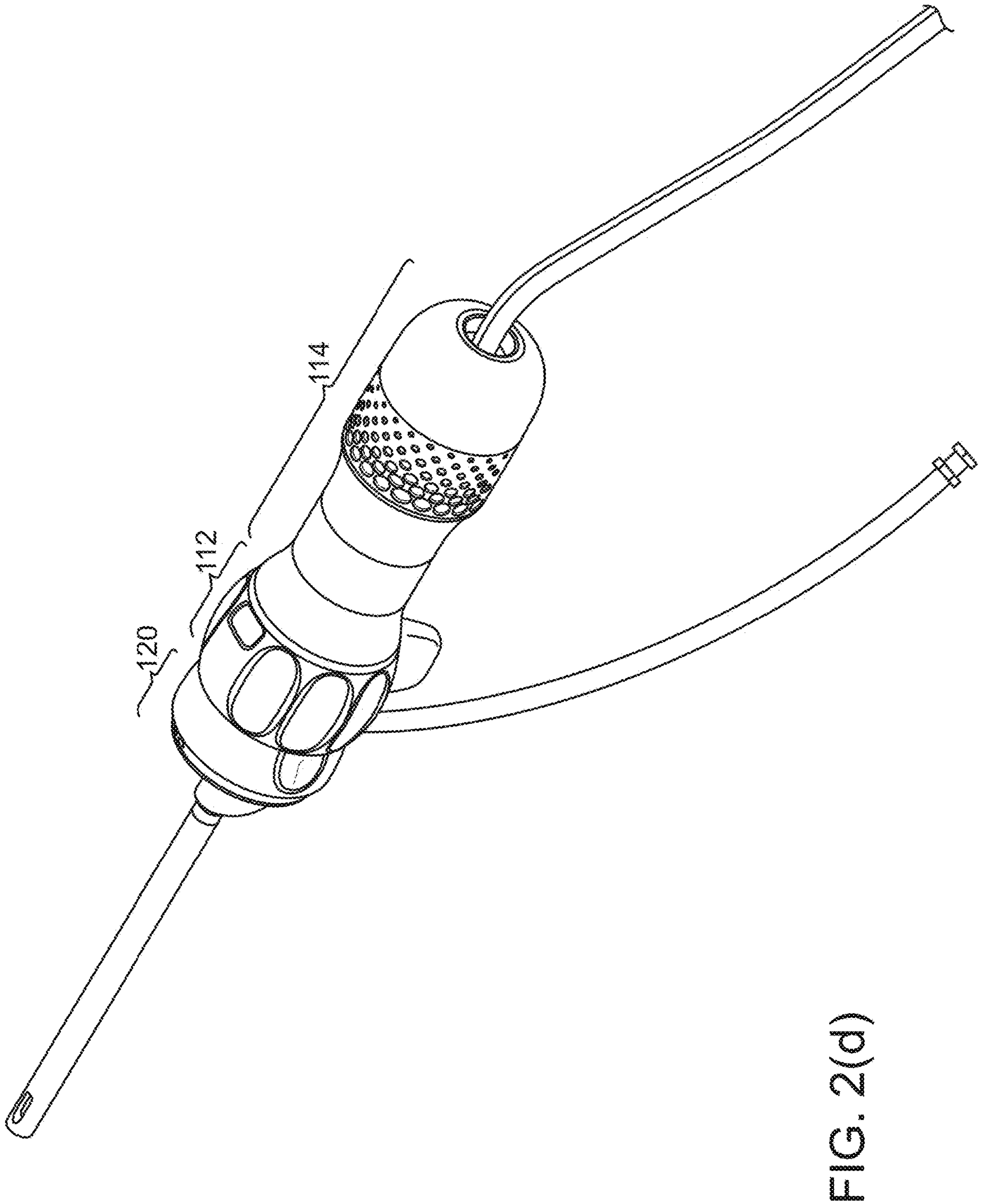
Figure 3A:
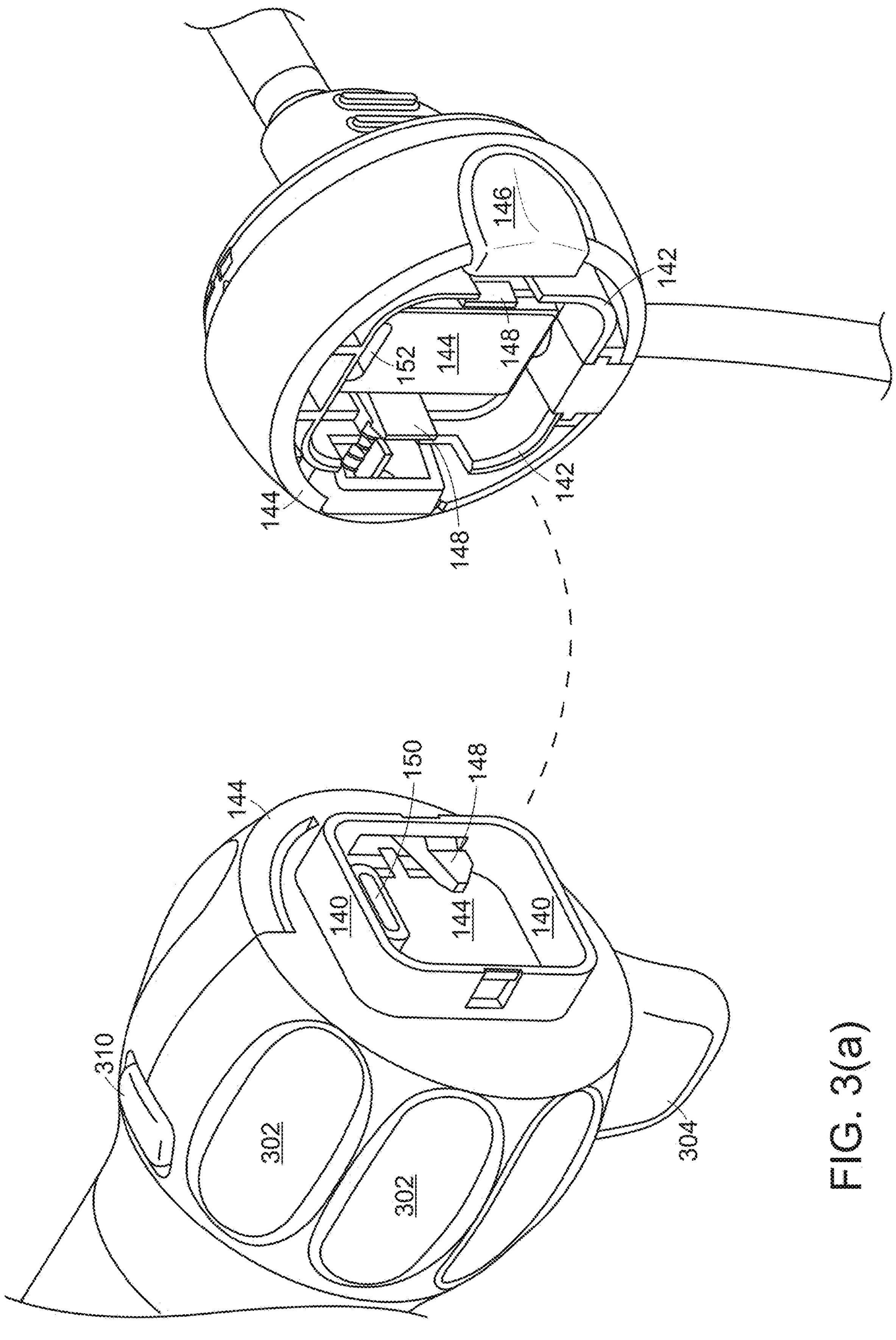
FIGS. 3(*b*), 3(*c*), 3(*d*), 3(*f*), 4(*b*), 4(*c*), 4(*d*), and 5(*c*) show endoscopes, partially cut away.
Figure 3B:
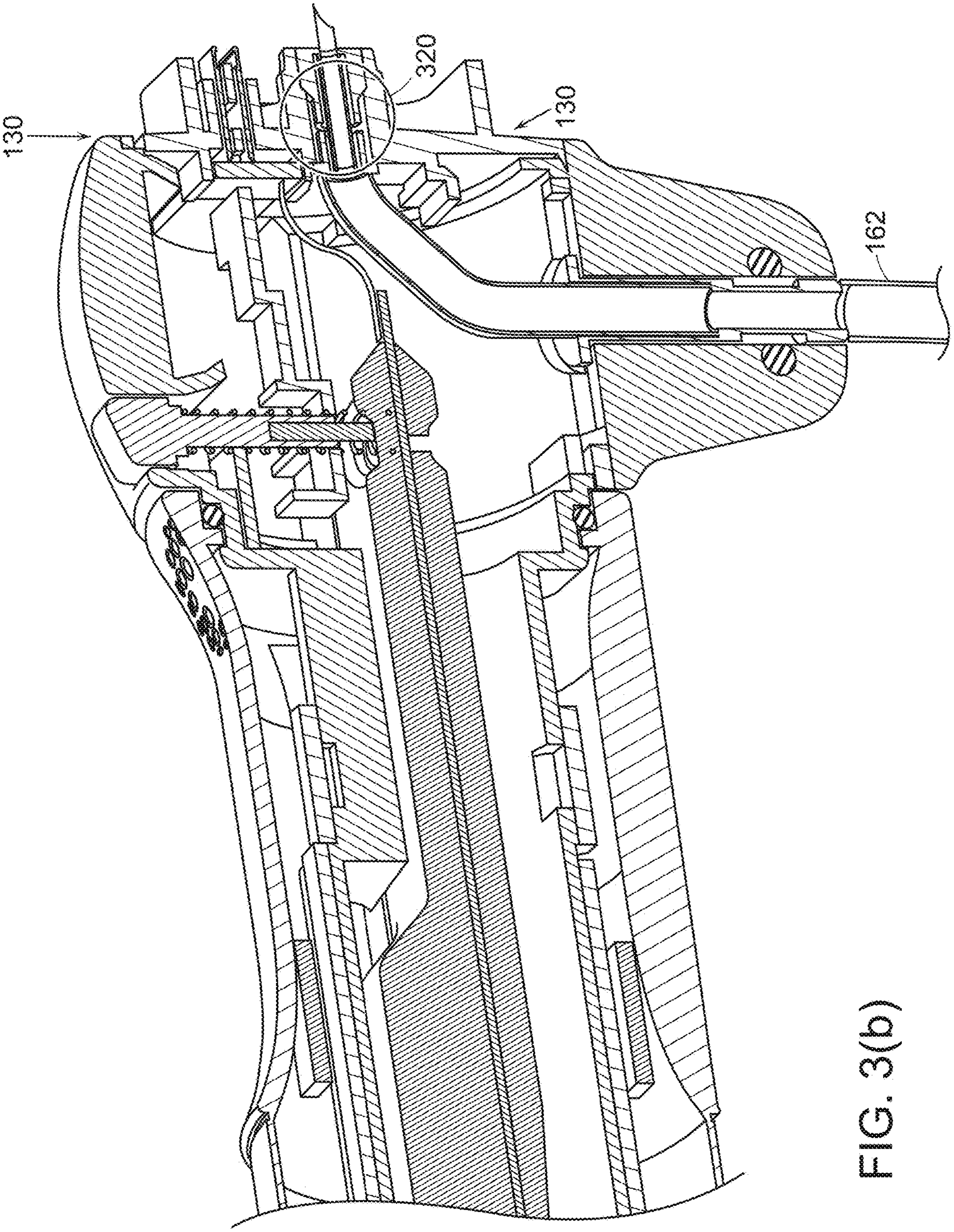
Figure 3C:
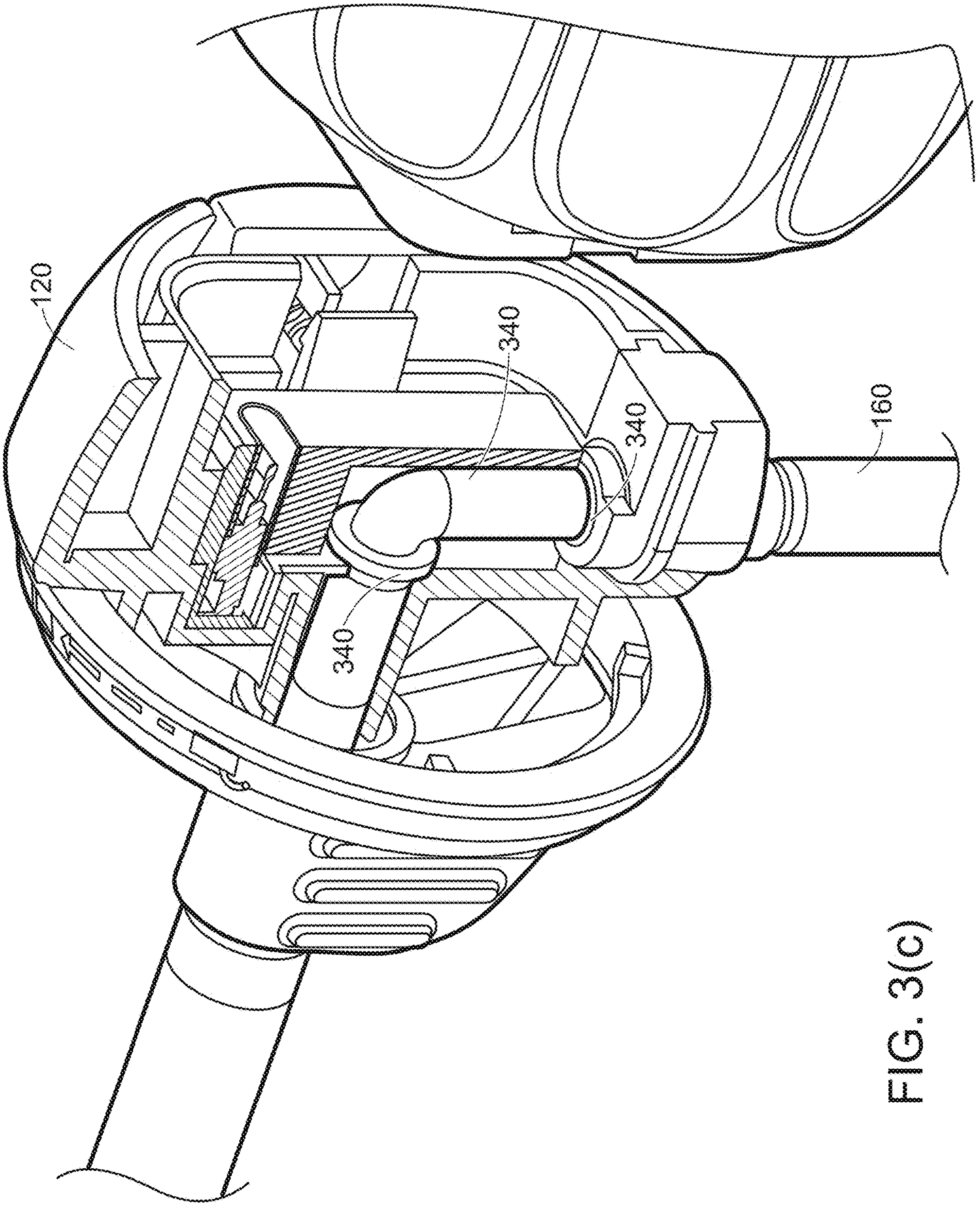
Figure 3D:
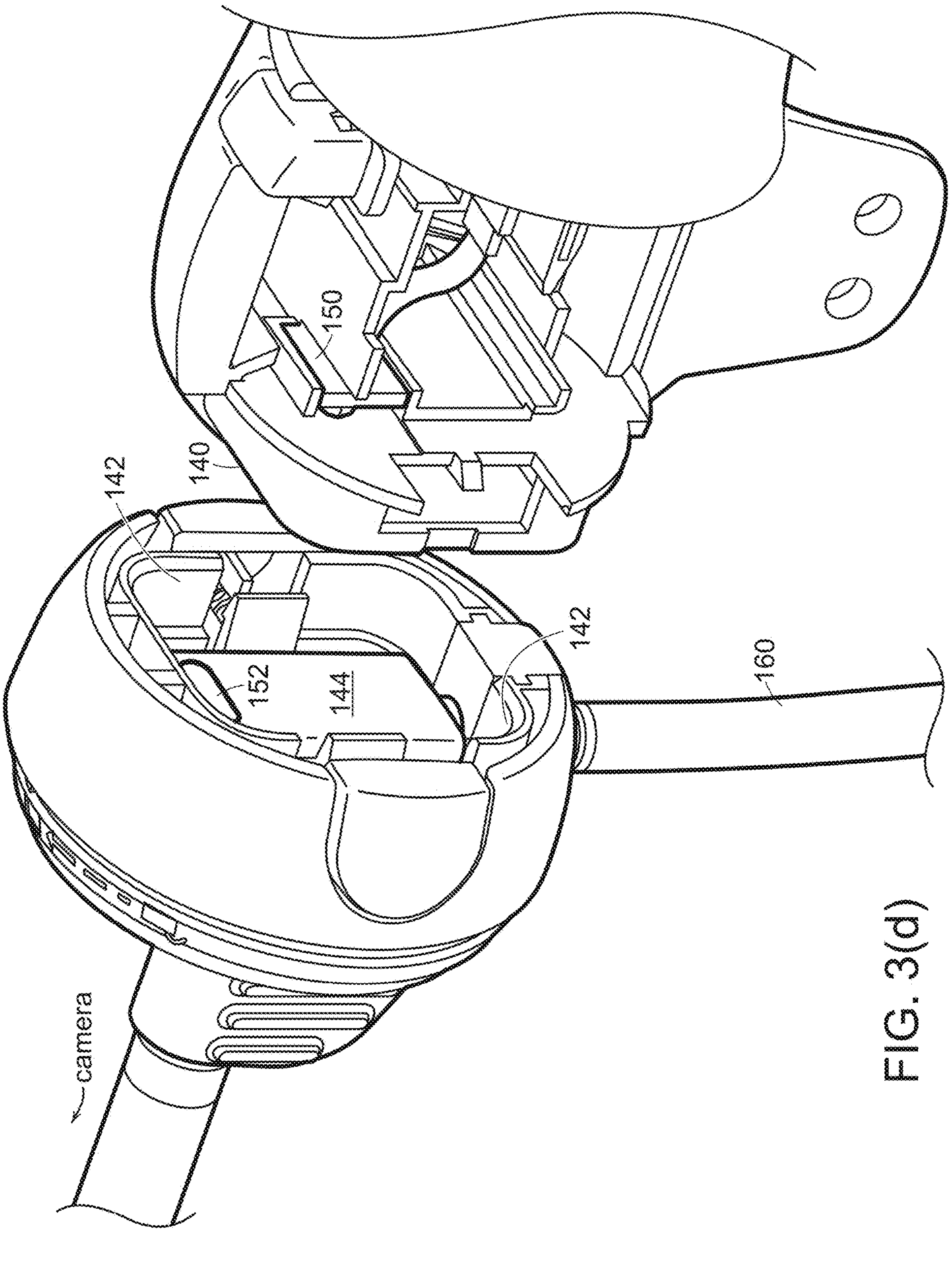
Figure 3E:
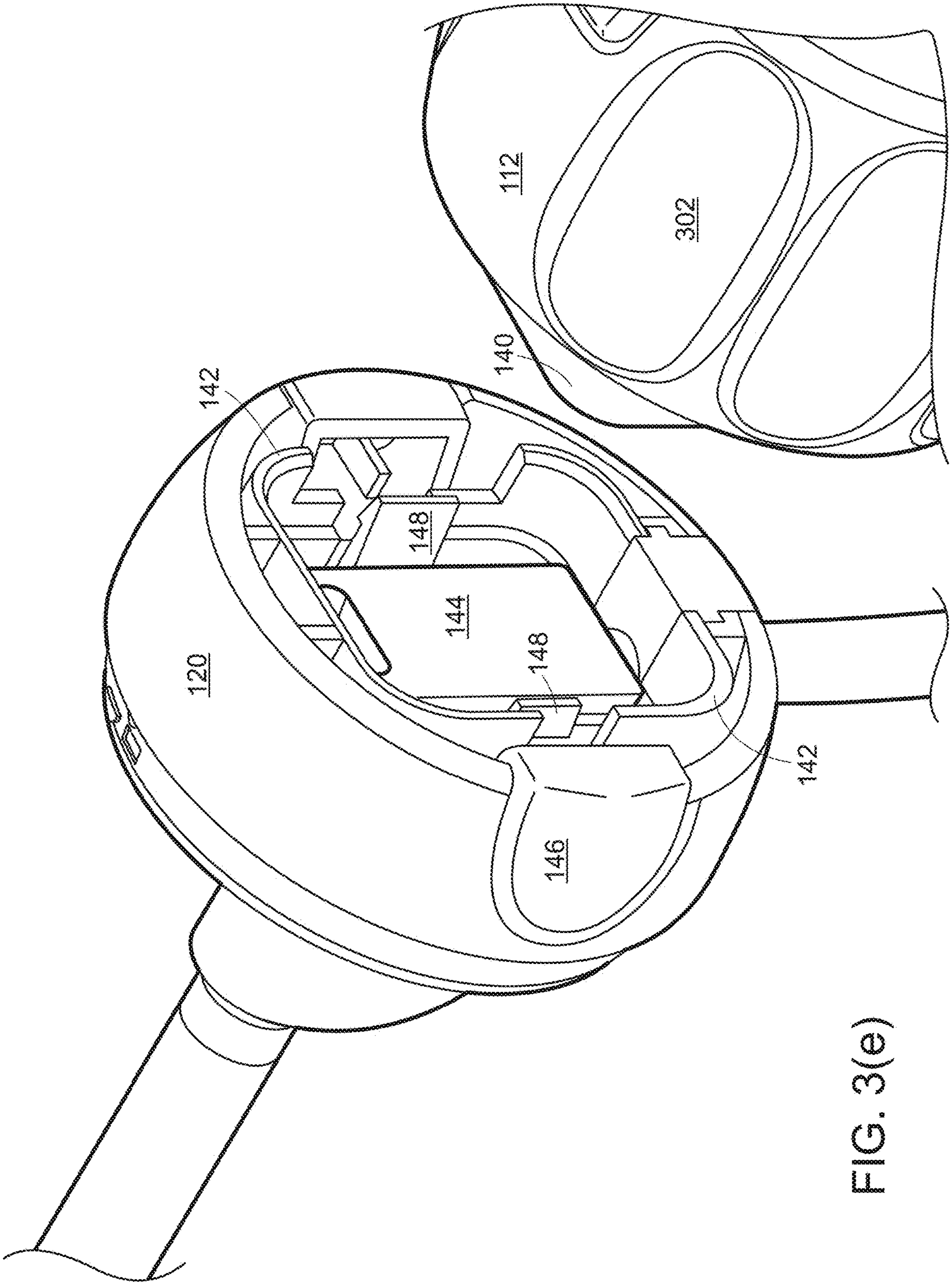
Figure 3F:
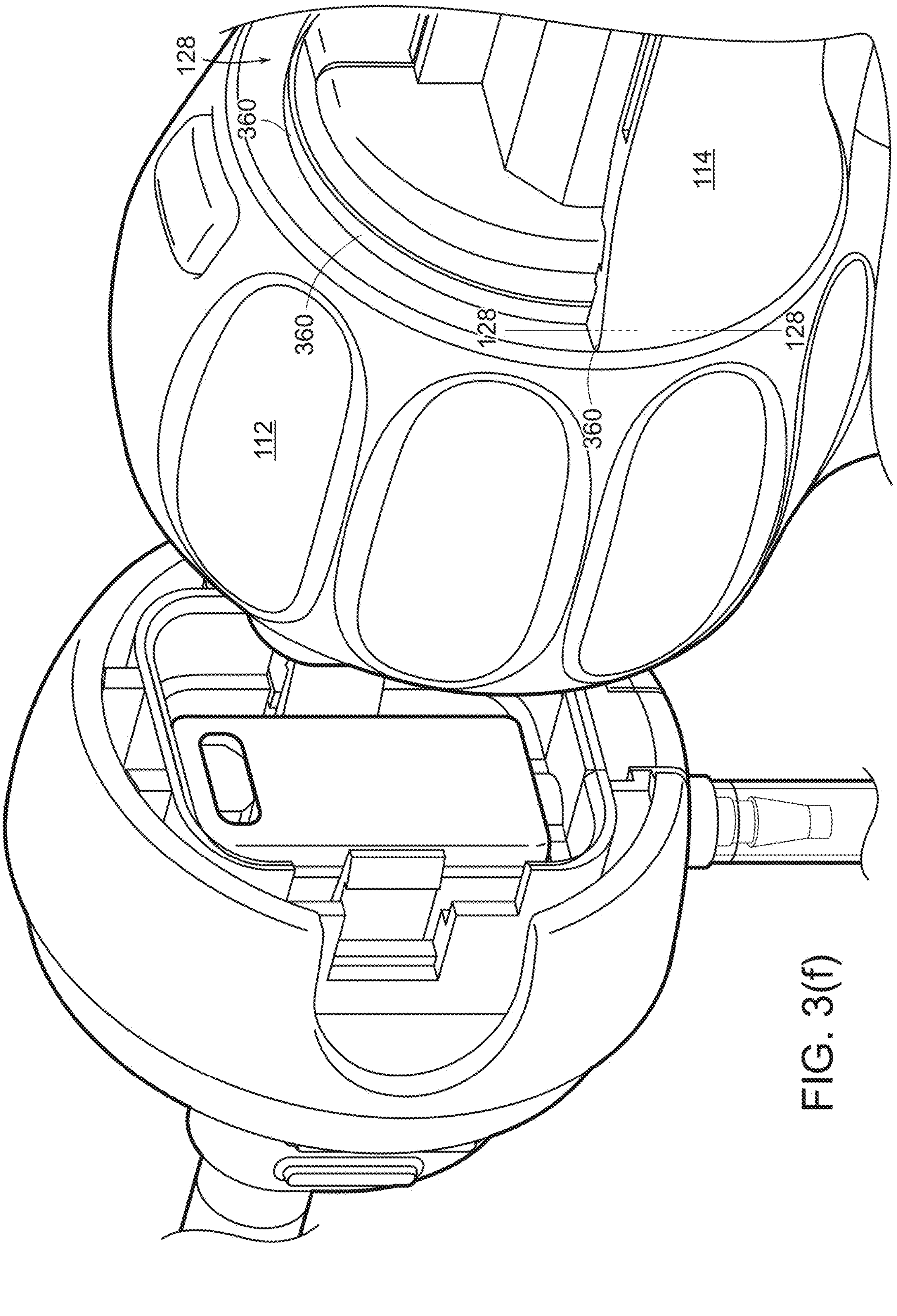
Figure 3G:
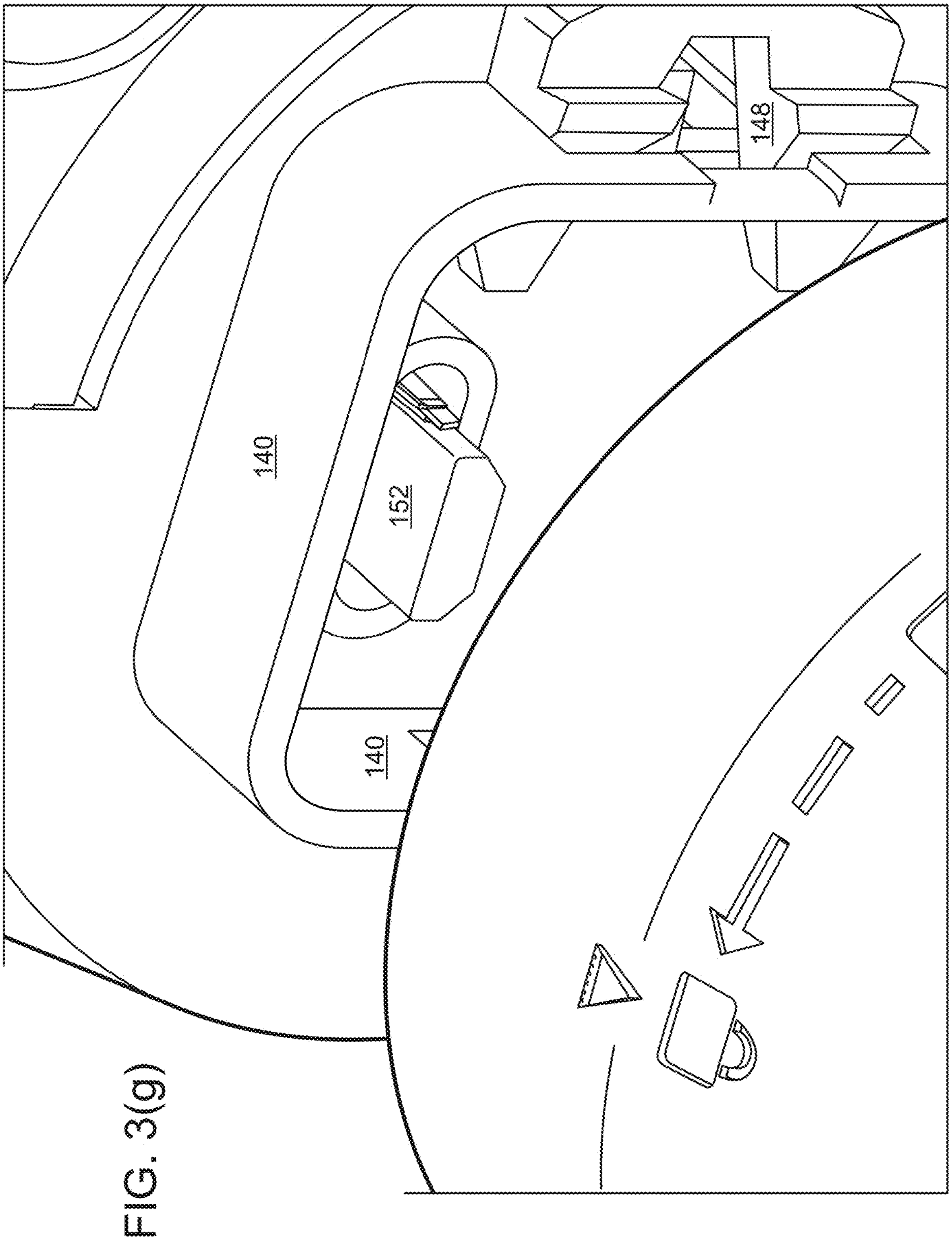
Figure 4A:
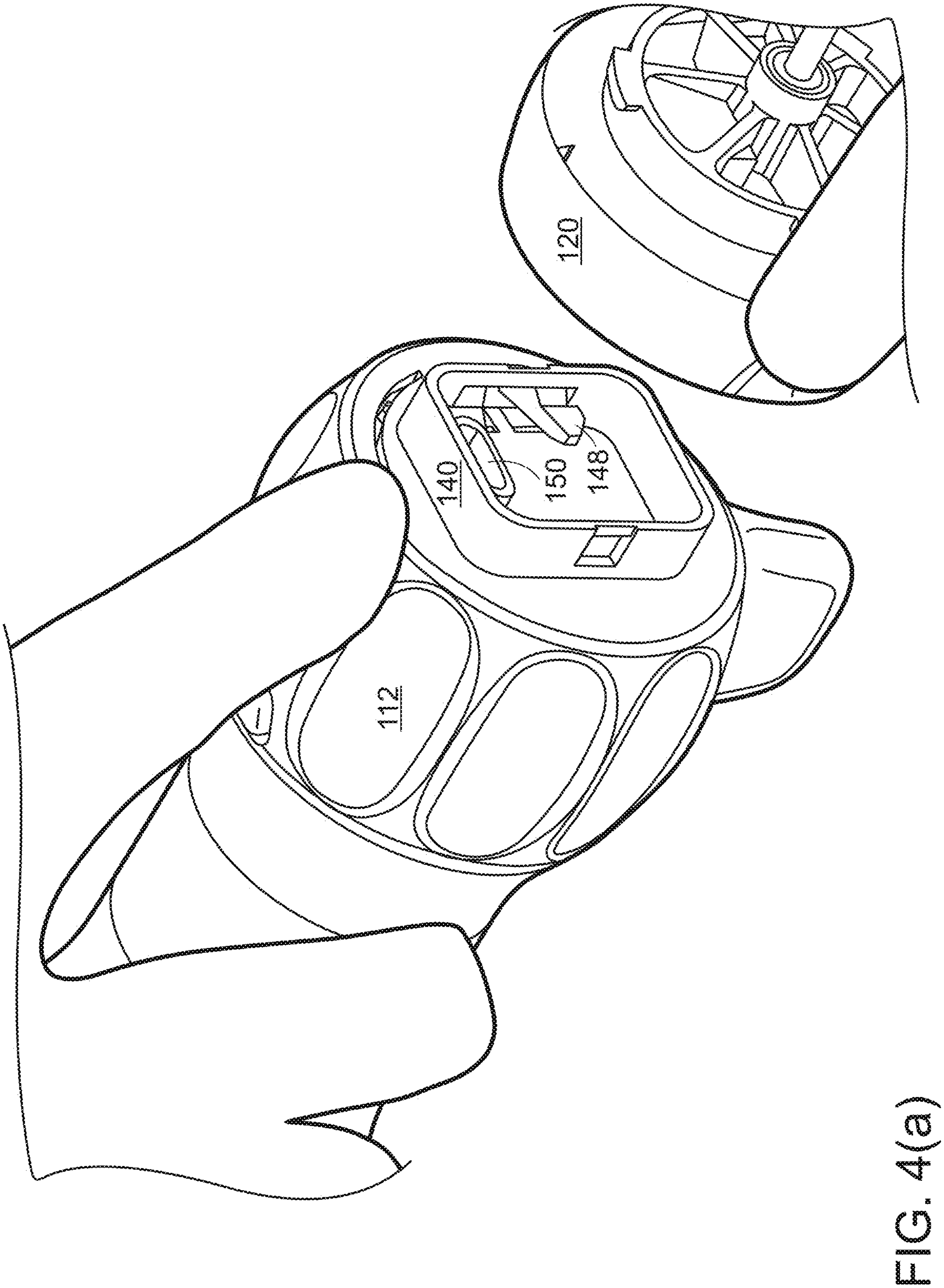
Figure 4B:
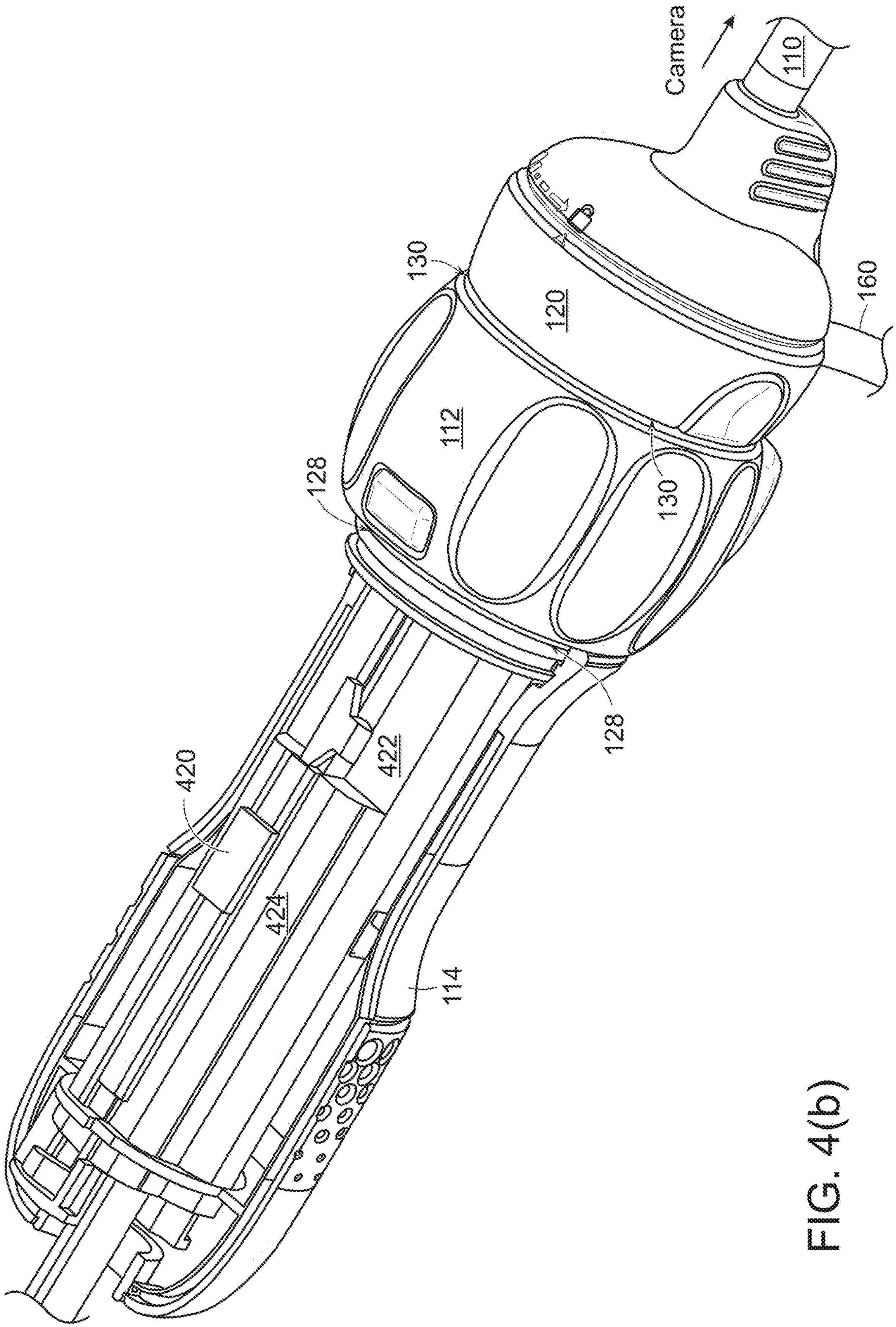
Figure 4C:
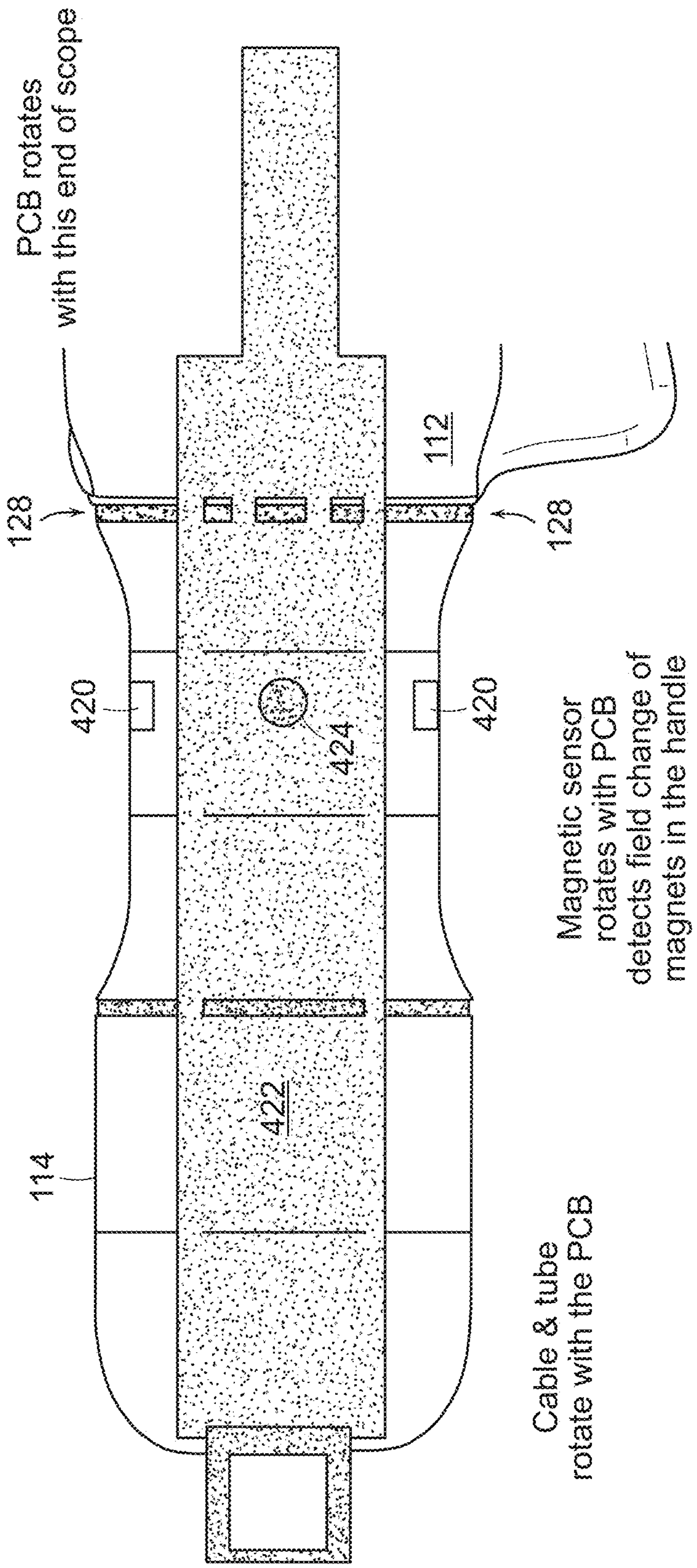
Figure 4D:
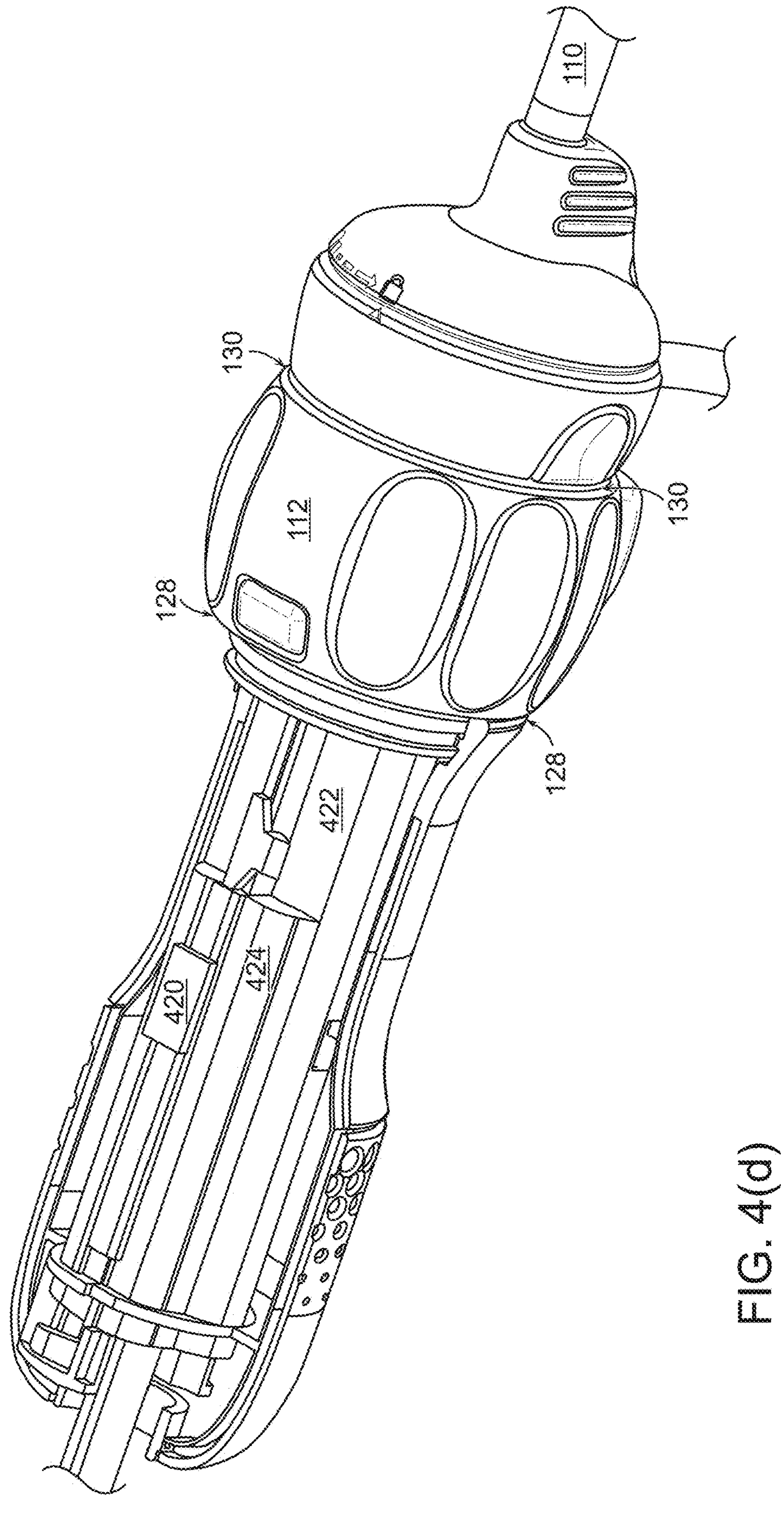
Figure 5A:
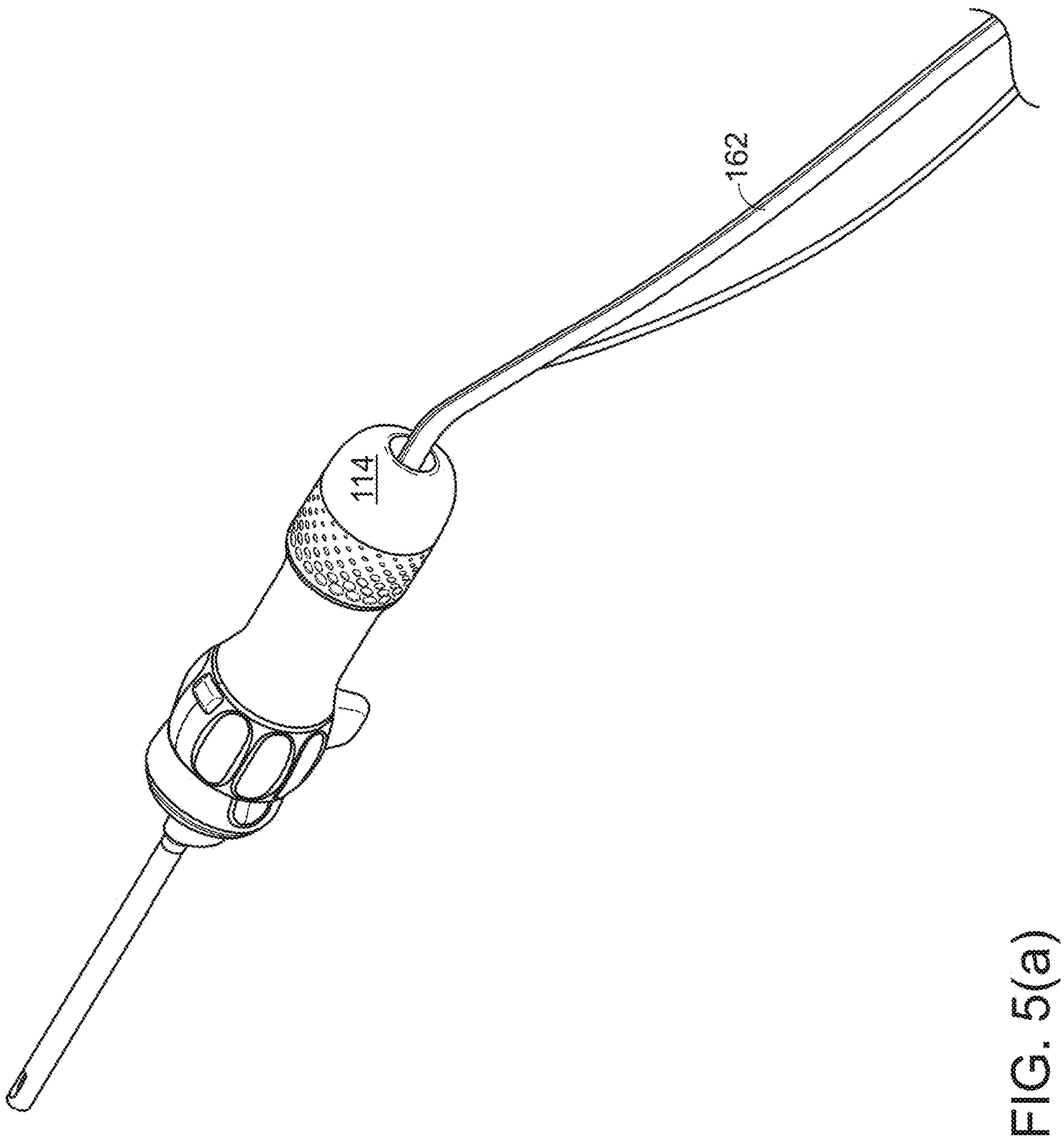
Figure 5B:
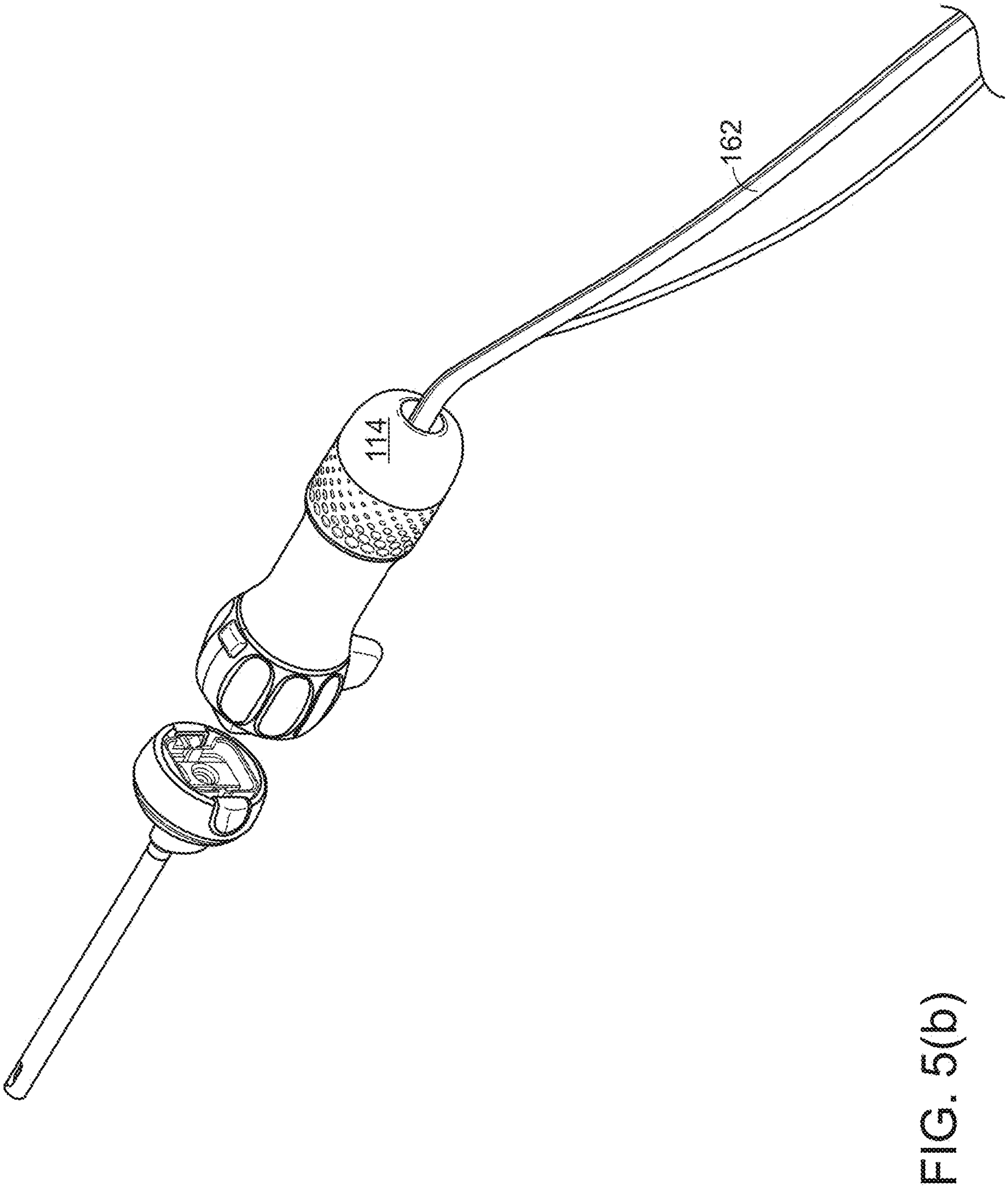
Figure 5C:
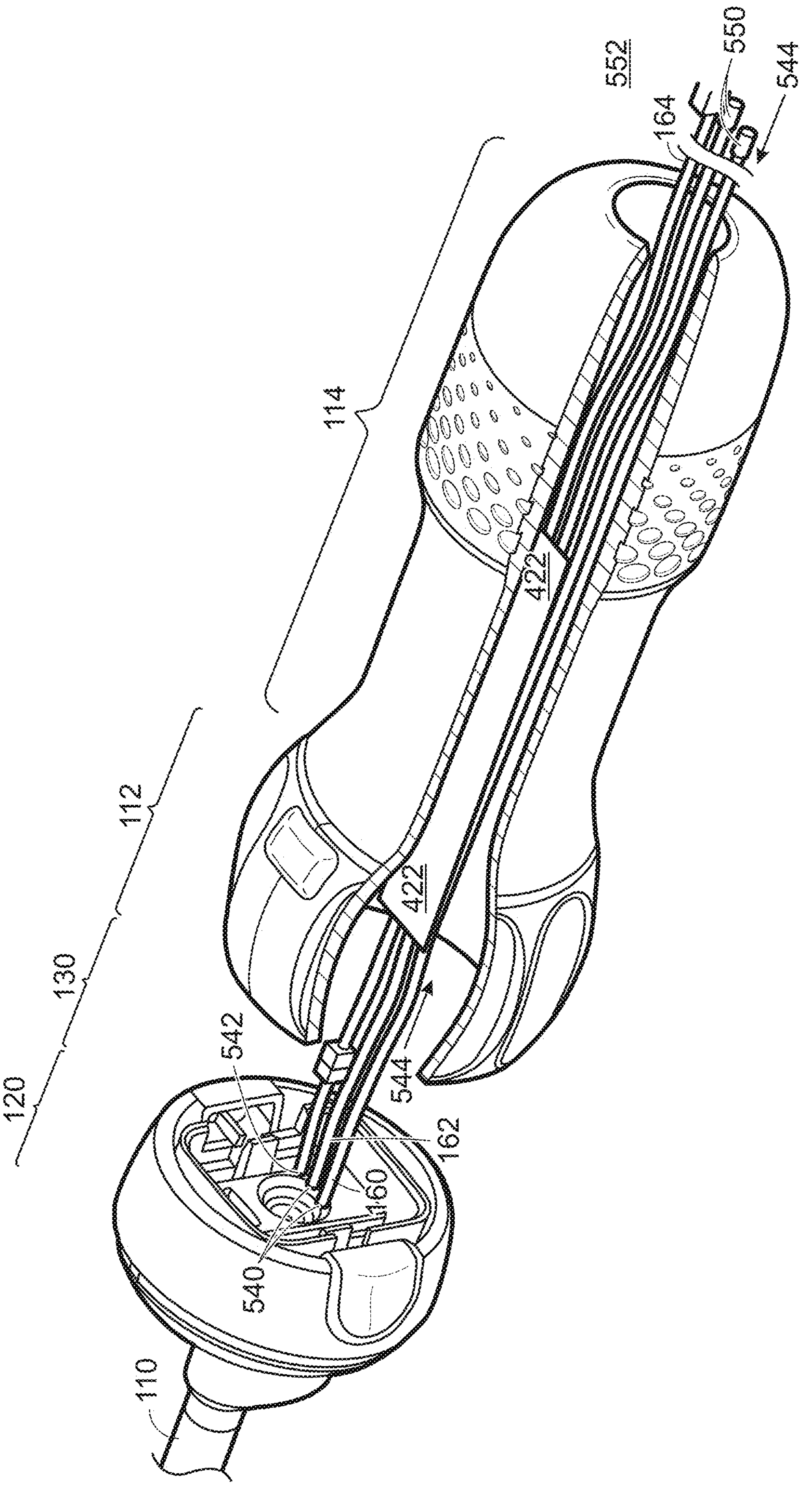
Figure 5D:
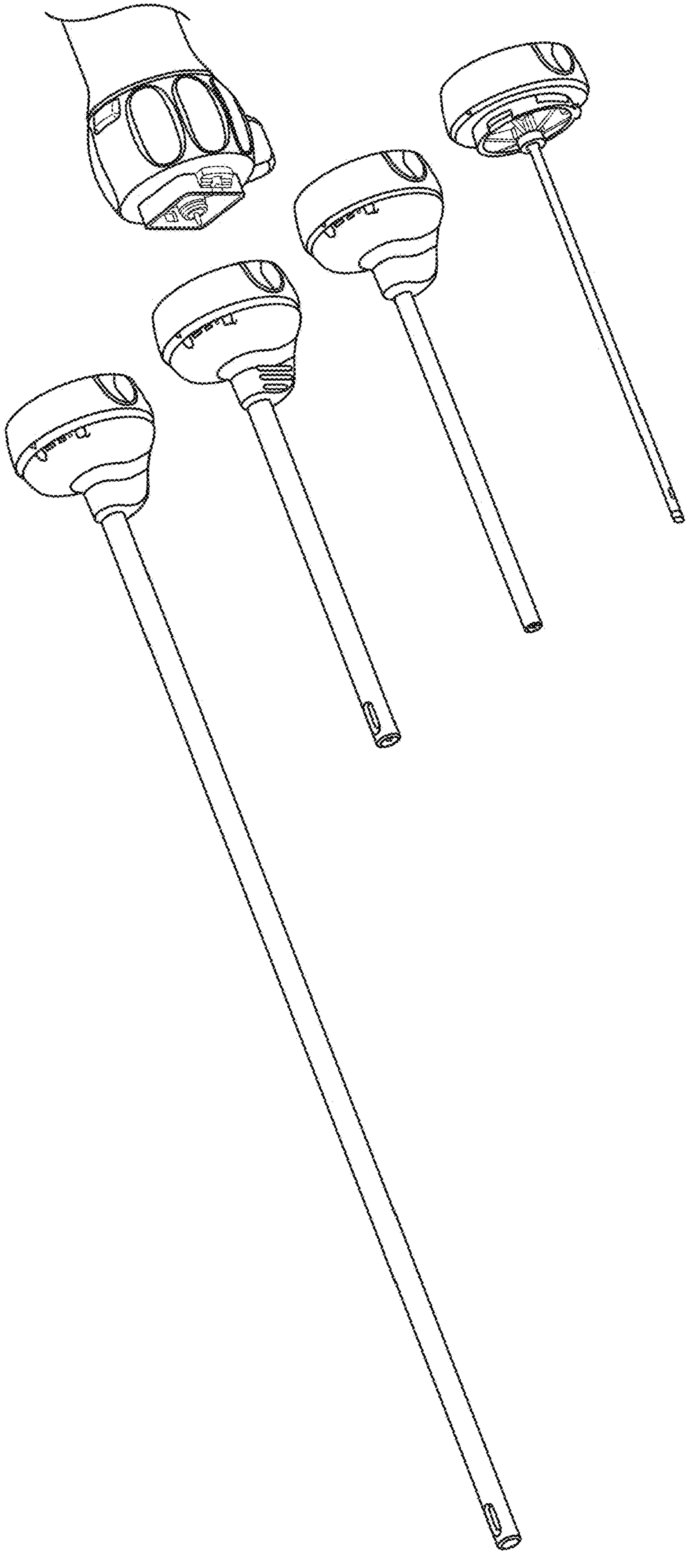

Referring to FIGS. 2(*a*), 2(*b*), 2(*c*), and 2(*d*), the endoscope may have a handle 112, 114, 120, and a shaft 110 for insertion into a body. At or near distal tip 116 of the shaft 110 may be a camera, electronic image sensor, or other optical component. The camera's orientation may be fixed in the scope, or may be pannable. The camera may be at tip 116, looking out from the shaft, or may be recessed a short distance behind the structural tip of the shaft. Also at or near the tip may be an illumination source, such as an LED. Tip 116 may have a rigid pointed tocar tip, or may have a spoon-shaped portion that reaches past the image sensor, or may be flexible (in the manner of the tip of a colonoscope), in each case extending a little beyond imaging camera to provide physical protection to the camera/image sensor during insertion or to protect the camera/image sensor from a surgical cutting device.

Illumination may be in visible light, infrared, and/or ultraviolet. In some cases, the illumination LED (light emitting diode) may be placed in reusable handle 112, 114, and the disposable shaft may have fiber optics to transmit light to the tip, and joint 130 may have an optical coupler. In other cases, the illumination LED may be placed in tip 116 to illuminate the surgical cavity directly; in such cases, joint 130 may have a power connector. In some cases, the LED may be recessed from the tip, or placed somewhere in the shaft, and optical fiber may carry illumination light to the tip. The optical fiber may be configured, for example, with a split, so that light will be arrayed in a desired pattern around the image sensor to better distribute the light into the surgical cavity around the image sensor.

The shaft 110 itself may be rigid, made of a nonbioreactive metal such as stainless steel or coated aluminum. In some cases, a surgical cavity around the endoscope tip may be insufflated by gas (typically carbon dioxide), or irrigated by saline solution. In either case, fluid inflow and outflow may be effected by channels through the shaft.

Shaft 110 may also carry power wires to the illumination LED and the camera, and carry signal wires that carry an optical signal back from the camera to electronics in the reusable portion 112, 114 of the handle. Electrical power to the camera may be supplied over conductors in a flexible cable or on a printed circuit board (flexible or rigid), and insulated with a conformal and insulating coating such as parylene. This same flexible circuit board may have signal conductors for the video signal from the camera. The video signal may be transmitted from the camera to the handle using any video signal protocol, for example, MIN (Mobile Industry Processor Interface) or HDMI. Parylene may also improve biocompatibility.

Shaft 110 may also carry cables or other mechanical elements to control panning of the camera.

Referring to FIG. 3(*a*), rotation collar may have various features that make rotation easy. For example, depressions 302 may provide a good grip for fingers for light roll torque. Fin 304 may provide greater leverage for greater roll torque, and may also provide a fixed rotational point of reference.

A button 310 may perform various functions, such as turning illumination LED on or off, taking pictures, starting and stopping video, and the like. A single button may perform all these functions based on the nature of the press. For example, press-and-hold for 3 seconds may turn the illumination LED on and off. A quick press may capture a single-frame still picture. A double-click may start and stop video recording.

If the camera at the tip 116 of shaft 110 is pannable or has other controllable features, there may be a control (for example, a lever, or a touch-slide panel, etc.) near button 310 to control that adjustment of the camera.

One or more ultraviolet LEDs may be placed inside handle 112,114, inside shaft 110, or near tip 116 to assist with insuring sterility of the internal components of the device or of the water as it passes thru the device Referring to FIG. 3(*b*), irrigation/insufflation hose(s) 160, 162 may enter at various points through the handle. For example, irrigation/insufflation hose(s) 160, 162 may enter through fin 304. Or, as shown in FIGS. 5(*a*), and 5(*b*), irrigation/insufflation fluid/gas hose(s) 160, 162 may enter through the proximal end of handle 114. This hose may then be disconnectable via a fluid disconnect joint 320 within joint 130. Referring to FIG. 3(*c*), in cases where hose(s) 160 for insufflation fluid/gas enters through disposable cap 120, various joints and strain relief features 340 may be used to hold hose(s) 160 in place.

Referring to FIG. 3(*d*) and FIG. 3(*g*), electrical connectors 150, 152 such as USB-C or mini-HDMI connectors may be used to connect the camera to a circuit board interior to handle 114.

Referring to FIG. 3(*e*), rotation-locking coupling 140, 142 may lock disposable cap 120 in rotational relationship to rotation collar 112. Various rigid and resilient features 144, 148 may lock them together for other forces and torques, and release buttons 146 may permit them to disengage to allow replacement of disposable cap 120.

Referring to FIG. 3(*f*), rotation between the handle's stationary portion 114 and rotation collar 112 may be provided via a rotational bearing 360 at joint 128.

Referring to FIGS. 4(*b*) and 4(*c*), proximal handle 114 may contain a number of components, typically components that have only incidental patient contact (and therefore present less risk of cross-infection), are higher in cost (and therefore desirably reusable), and either sterilizable or may be covered by a sterility sleeve. For example, proximal handle 114 may hold power transformers, signal amplifiers, controls for the illumination LED and camera, a mechanical control for panning the camera, rotation sensors for righting of an image from the camera, and the like. The handle may also include connections to external sources and destinations of power, signal, fluid, and the like.

Proximal handle 114 may include rotational sensors so that an angular orientation of the camera may be ascertained. For example, the inner surface of proximal handle 114 may mount one or more magnets 420, and printed circuit board 422 (which rotates with rotation collar 112 and disposable cap 120) may have sensors 424 that detect the magnets. This may be used to compute a rotational orientation, which may in turn be used to "right" the image from the camera on a video display screen.

The distal tip of the shaft, the camera mounted therein, and the mounting of componentry within the shaft may be designed to be robust. Occasionally, during surgery, the tip of the endoscope may come into contact with a shaver, ablation probe, or cauterization probe, and it may be desirable to have the tip be robust to such contacts. To reduce risk that componentry may be dislodged and left in the patient, the disposable shaft and its componentry may be designed to avoid joints that are at high risk of mechanical failure. A disposable optical system may prevent the image degradation that occurs when nondisposable optics are reused in multiple surgical procedures.

Endoscopes as a genus include arthroscopes, laparoscopes, colonoscopes, and other specialized scopes for various body cavities. For an arthroscope for joint surgery, the shaft may be as small as 5 mm, 5.5 mm, or 6 mm, and highly rigid. For other endoscopes, such as a colonoscope, the diameter may be larger, and the shaft may be flexible.

The endoscope may be delivered as a handle and multiple tips, each tip individually sealed for sterility.

Figure 6:
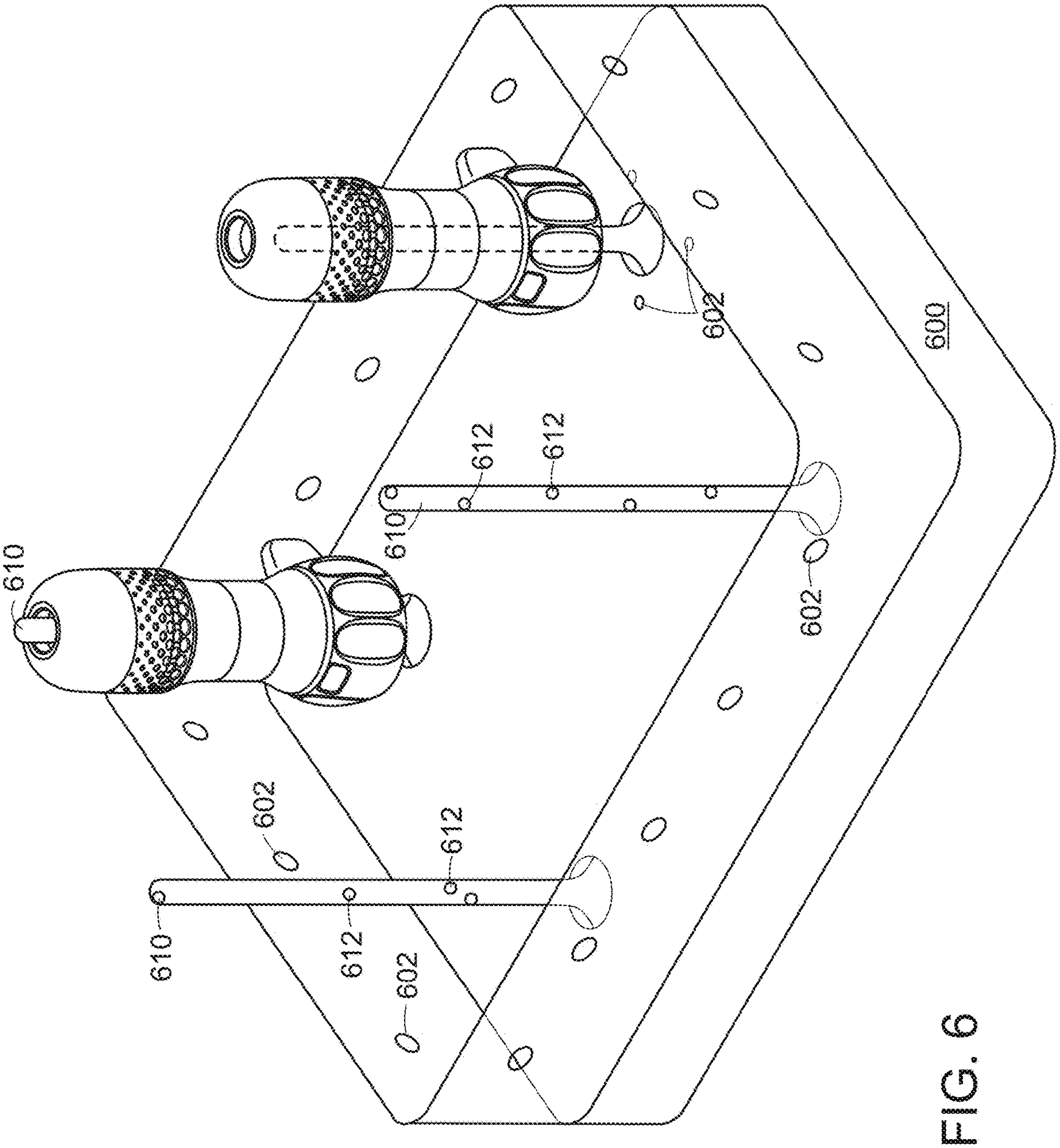
FIG. 6 is a perspective view of endoscope handles in a sterilizer.

Referring to FIG. 6, reusable handles 112, 114 may be sterilized in a sterilizer 600. Preferably, hose(s) 160, 162 and all other portions of endoscope 100 that come into contact with the patient, or with fluids that have come into contact with the patient, are disposable, and the design for reusable portions 112, 114 ensures that contamination is minimized through avoiding contact with the patient's bodily fluids. Sterilizer 600 may be arranged to accept one or more reusable handles 112, 114, and irradiate them with ultraviolet light from ultraviolet LEDs 602. Rods 610 that pass through handle channel 544 may have ultraviolet LEDs 612 arranged along their lengths, to sterilize internal channels 544.

IV. Other Embodiments

Various processes described herein may be implemented by appropriately programmed general purpose computers, special purpose computers, and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in one or more computer programs, one or more scripts, or in other forms. The processing may be performed on one or more microprocessors, central processing units (CPUs), computing devices, microcontrollers, digital signal processors, or like devices or any combination thereof. Programs that implement the processing, and the data operated on, may be stored and transmitted using a variety of media. In some cases, hard-wired circuitry or custom hardware may be used in place of, or in combination with, some or all of the software instructions that can implement the processes. Algorithms other than those described may be used.

Programs and data may be stored in various media appropriate to the purpose, or a combination of heterogenous media that may be read and/or written by a computer, a processor or a like device. The media may include non-volatile media, volatile media, optical or magnetic media, dynamic random access memory (DRAM), static ram, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge or other memory technologies.

Databases may be implemented using database management systems or ad hoc memory organization schemes. Alternative database structures to those described may be readily employed. Databases may be stored locally or remotely from a device which accesses data in such a database.

In some cases, the processing may be performed in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Transmission media include coaxial cables, copper wire and fiber optics, including the wires that comprise a system bus coupled to the processor. Transmission may occur over transmission media, or over electromagnetic waves, such as via infrared, WiFi, Bluetooth, and the like, at various frequencies using various protocols. Each of the devices may themselves comprise computers or other computing devices, such as those based on the Intel® Pentium® or Centrino™ processor, that are adapted to communicate with the computer. Any number and type of devices may be in communication with the computer.

A server computer or centralized authority may or may not be necessary or desirable. In various cases, the network may or may not include a central authority device. Various processing functions may be performed on a central authority server, one of several distributed servers, or other distributed devices For the convenience of the reader, the above description has focused on a representative sample of all possible embodiments, a sample that teaches the principles of the invention and conveys the best mode contemplated for carrying it out. Throughout this application and its associated file history, when the term "invention" is used, it refers to the entire collection of ideas and principles described; in contrast, the formal definition of the exclusive protected property right is set forth in the claims, which exclusively control. The description has not attempted to exhaustively enumerate all possible variations. Other undescribed variations or modifications may be possible. Where multiple alternative embodiments are described, in many cases it will be possible to combine elements of different embodiments, or to combine elements of the embodiments described here with other modifications or variations that are not expressly described. A list of items does not imply that any or all of the items are mutually exclusive, nor that any or all of the items are comprehensive of any category, unless expressly specified otherwise. In many cases, one feature or group of features may be used separately from the entire apparatus or methods described. Many of those undescribed variations, modifications and variations are within the literal scope of the following claims, and others are equivalent.

The invention claimed is:

1. An endoscope, comprising:

a handle and a first insertion shaft;

the first insertion shaft having an illumination emitter and a solid state imaging sensor at or near a distal tip of the shaft, the illumination emitter and imaging sensor designed to provide illumination and imaging of an interior of a body cavity for a surgeon during surgery;

a proximal portion of the handle having electronics designed to drive the illumination emitter and to receive an imaging signal from the imaging sensor, the proximal handle portion being designed to permit sterilization of the proximal handle portion between uses;

a separation joint between the proximal handle portion and the first insertion shaft, the separation joint having handle portions attached to the proximal handle portion and insertion shaft portions attached to the first insertion shaft designed to separably connect the first insertion shaft to the proximal handle portion:

when the handle portions and the insertion shaft portions are separated, the separation joint permitting removal of the first insertion shaft for disposal and replacement of the first insertion shaft; and when the handle portions and the insertion shaft portions are connected, the separation joint designed to provide mechanical force transfer applied by a surgeon's hand to the first insertion shaft, the separation joint designed to transfer roll torques, the separation joint having a lock designed to lock the first insertion shaft and proximal handle portion of the endoscope to each other, the separation joint having facing flat force-transmittal surfaces at or near a periphery of the separation joint that, when the separation joint is connected and locked, abut flat force-transmittal surfaces of the first insertion shaft at or near a periphery of the first insertion shaft to transmit insertion and withdrawal forces across the separation joint, the separation joint's lock and peripheral flat force-transmittal surfaces designed to provide stiffness in bending across the separation joint to transfer pitch and yaw torques across the separation joint, the separation joint having an electrical connector designed to provide separable electrical connectivity between the proximal handle electronics and the illumination emitter and imaging sensor;

the separation joint designed to bring the peripheral flat force-transmittal surfaces together via a motion compatible with connection of the electrical connector the separation joint designed to permit removal of the first insertion shaft for disposal and replacement, the first insertion shaft having length and diameter dimensions; and the handle portions designed to reconnect a second insertion shaft at the separation joint, the second insertion shaft having at least one dimension, optical property, or configuration of the imaging sensor substantially different than the corresponding dimension, optical property, or sensor configuration of the first insertion shaft, the difference in dimension, optical property, or sensor configuration between the first and second insertion shafts specializing the first insertion shaft for surgery of organs of the body different than organs to which to second insertion shaft is specialized one or more ultraviolet LEDs internal to the endoscope and designed to sterilize a region of an interior of the endoscope.

2. The endoscope of claim 1, further comprising:

a rotation joint between the proximal handle portion and the first or second insertion shaft designed to permit rotation of the insertion shaft relative to the proximal handle portion in a roll dimension about a central axis of the insertion shaft.

3. The endoscope of claim 1, further comprising:

the difference in dimension, optical property, or sensor configuration between the insertion shafts specializing the first and second shafts, respectively, to different types of surgery.

4. An endoscope, comprising:

a handle and an insertion shaft;

the insertion shaft having an illumination emitter and a solid state imaging sensor at or near a distal tip of the shaft, the illumination emitter and imaging sensor designed to provide illumination and imaging of an interior of a body cavity for a surgeon during surgery;

a proximal portion of the handle having electronics designed to drive the illumination emitter and to receive an imaging signal from the imaging sensor, the proximal handle portion being designed to permit sterilization of the proximal handle portion between uses;

a separation joint between the proximal handle portion and the insertion shaft, the separation joint having handle portions attached to the proximal handle portion and insertion shaft portions attached to the first insertion shaft designed to separably connect the insertion shaft to the proximal handle portion:

when the handle portions and the insertion shaft portions are separated, the separation joint permitting removal of the insertion shaft for disposal and replacement of the insertion shaft; and when the handle portions and the insertion shaft portions are connected, the separation joint designed to provide mechanical force transfer applied by a surgeon's hand to the insertion shaft, the separation joint designed to transfer roll torques, the separation joint having a lock designed to lock the insertion shaft and proximal handle portion of the endoscope to each other, the separation joint having facing flat force-transmittal surfaces at or near a periphery of the separation joint that, when the separation joint is connected and locked, abut to transmit insertion and withdrawal forces across the separation joint, the separation joint's lock and peripheral flat force-transmittal surfaces designed to provide stiffness in bending across the separation joint to transfer pitch and yaw torques across the separation joint, the separation joint having an electrical connector designed to provide separable electrical connectivity between the proximal handle electronics and the illumination emitter and imaging sensor;

the separation joint designed to bring the peripheral flat force-transmittal surfaces together via a motion compatible with connection of the electrical connector;

one or more ultraviolet LEDs internal to the endoscope and designed to sterilize a region of an interior of the endoscope.

5. The endoscope of claim 4, wherein:

the insertion shaft comprises a first insertion shaft and a second insertion shaft; and the separation joint is designed to permit removal of the first insertion shaft for disposal and replacement, and the handle portions designed to reconnect the second insertion shaft at the separation joint, the second insertion shaft having at least one dimension, optical property, or configuration of the optical sensor substantially different than the corresponding dimension, optical property, or sensor configuration of the first insertion shaft, the difference in dimension, optical property, or sensor configuration between the first and second insertion shafts specializing the first insertion shaft for surgery of organs of the body different than organs to which to second insertion shaft is specialized.

6. The endoscope of claim 4, wherein:

the insertion shaft comprises two or more insertion shafts; and pairs of the two or more insertion shafts having at least one dimension, optical property, or configuration of the optical sensor different than the corresponding dimension, optical property, or sensor configuration of the other, the different dimension, optical property, or sensor configuration specializing the respective insertion shafts to different surgical procedures, the insertion shaft connectable to the proximal handle portion at the handle portions of the separation joint, to permit use of the proximal handle portion in surgery with different requirements for the insertion shaft.

7. The endoscope of claim 4, further comprising:

a plurality of endoscope insertion shafts, each endoscope insertion shaft having an illumination emitter and a solid state imaging sensor at or near its respective tip, the illumination emitter and imaging sensor designed to provide illumination and imaging of an interior of a surgical cavity for a surgeon during surgery, the endoscope insertion shafts of the plurality having, respectively, differing dimensions, differing optical properties, or differently-configured imaging sensors at their respective tips, respectively specialized to different types of surgery.

8. An endoscope, comprising:

a handle and a plurality of insertion shafts;

the insertion shafts having respective illumination emitters and solid state imaging sensors at or near respective tips of respective shafts, the illumination emitters and imaging sensors designed to provide illumination and imaging of body cavities for a surgeon during surgery;

a proximal portion of the handle having electronics designed to drive the illumination emitter and to receive an imaging signal from the imaging sensor, the proximal handle portion being designed to permit sterilization of the proximal handle portion between uses, and having one or more ultraviolet LEDs internal to the endoscope and designed to sterilize a region of an interior of the endoscope;

the endoscope insertion shafts of the plurality having, respectively, differing dimensions, differing optical properties, or differently-configured imaging sensors at their respective tips, respectively specialized to surgery of different organs of the body;

a separation joint having handle portions at the distal end of the proximal handle portion, the handle portions designed to permit removal of a first one of the plurality of insertion shafts for disposal and replacement and, to reconnect a second one of the plurality of insertion shafts, and to separably connect a respective one of the insertion shafts to the proximal handle portion at the separation joint;

the separation joint permitting removal of the first one of the plurality of insertion shafts for disposal and replacement the separation joint designed to provide mechanical force transfer applied by a surgeon's hand to the connected insertion shaft, the separation joint having roll torque transfer means for transferring roll torques, the separation joint having locking means for locking the connected insertion shaft and proximal handle portions of the endoscope to each other, the separation joint having flat force-transmittal means, surfaces at or near a periphery of the separation joint that, when the separation joint is connected and locked, abut flat force-transmittal means, surfaces at or near a periphery of the one of the plurality of the insertion shafts, of one of the plurality of insertion shafts to transmit insertion and withdrawal forces across the separation joint, the separation joint's locking means and peripheral flat force-transmittal surfaces designed to provide stiffness in bending across the separation joint to transfer pitch and yaw torques across the separation joint, the separation joint having an electrical connector designed to provide separable electrical connectivity between the proximal handle electronics and the illumination emitter and imaging sensor;

mechanical means of the separation joint designed to bring the peripheral flat force-transmittal surfaces together via a motion compatible with connection of the electrical connector;

the handle having a rotation collar having surface means for assisting the surgeon in rotating the first one of the plurality of insertion shaft in a roll dimension about a central axis of the insertion shaft relative to the proximal handle portion.

9. The endoscope of claim 8, wherein:

the handle further has a distal portion lying between the respective one of the insertion shafts and proximal handle portion, the respective one of the insertion shafts being rigidly affixed to the distal handle portion, and the separation joint being disposed to connect and disconnect the distal and proximal portions of the handle;

the distal handle portion designed to indirectly transfer mechanical force between a surgeon's hand to the respective one of the insertion shafts, and provide indirect electrical connectivity from the proximal handle electronics to the illumination emitter and imaging sensor.

10. An endoscope, comprising:

a handle and a plurality of endoscope insertion shafts;

each endoscope insertion shaft having an illumination emitter and a solid state imaging sensor at or near its respective tip, the illumination emitter and imaging sensor designed to provide illumination and imaging of an interior of a surgical cavity for a surgeon during surgery, the endoscope insertion shafts of the plurality having, respectively, differing dimensions, differing optical properties, or differently-configured imaging sensors at their respective tips, the difference in dimension, optical property, or sensor configuration between the insertion shafts specializing the respective insertion shaft to, respectively, different types of surgery;

the handle having electronics designed to drive the illumination emitter and to receive an imaging signal from the imaging sensor, the handle being designed to permit sterilization of a proximal handle portion between uses;

a separation joint between the handle and an endoscope insertion shaft of the plurality of endoscope insertion shafts designed to separably connect the endoscope insertion shaft of the plurality of endoscope insertion shafts to the handle:

the separation joint having handle portions attached to the handle and insertion shaft portions respectively attached to each of the plurality of endoscope insertion shafts;

when the handle portions and the insertion shaft portions of the separation joint are separated, the separation joint permitting removal of the endoscope insertion shaft of the plurality of endoscope insertion shafts for disposal and replacement of the endoscope insertion shaft of the plurality of endoscope insertion shafts; and when the handle portions and one of the insertion shaft portions of the separation joint are connected, the separation joint designed to provide mechanical force transfer applied by a surgeon's hand to the endoscope insertion shaft of the plurality of endoscope insertion shafts, the separation joint having an electrical connector designed to provide separable electrical connectivity between the handle electronics and the imaging sensor; and one or more ultraviolet LEDs internal to the endoscope and designed to sterilize a region of an interior of the endoscope.

11. The endoscope of claim 10, wherein:

when the handle portions and one of the insertion shaft portions of the separation joint are connected, the separation joint designed to provide mechanical force transfer applied by a surgeon's hand to the insertion shaft of the plurality of endoscope insertion shafts, the separation joint designed to transfer roll torques, the separation joint having a lock designed to lock the insertion shaft and proximal handle portion of the endoscope to each other, the separation joint having facing flat force-transmittal surfaces at or near a periphery of the separation joint that, when the separation joint is connected and locked, abut to transmit insertion and withdrawal forces across the separation joint, the separation joint's lock and peripheral flat force-transmittal surfaces designed to provide stiffness in bending across the separation joint to transfer pitch and yaw torques across the separation joint.

12. The endoscope of claim 10, wherein:

the plurality of endoscope insertion shafts includes at least a first insertion shaft and second insertion shaft, separation joint designed to permit removal of the first insertion shaft for disposal and replacement, the first insertion shaft having length and diameter dimensions; and the handle portions of the separation joint designed to reconnect the second insertion shaft at the separation joint, the second insertion shaft having at least one dimension substantially different than the corresponding dimension of the first insertion shaft, the difference in dimension, optical property, or sensor configuration between the first and second insertion shafts specializing the first insertion shaft for surgery of organs of the body different than organs to which to second insertion shaft is specialized.

13. The endoscope of claim 10, further comprising:

a rotation joint between the handle and the endoscope insertion shaft of the plurality of endoscope insertion shafts designed to permit rotation of the endoscope insertion shaft of the plurality of endoscope insertion shafts relative to the handle in a roll dimension about a central axis of the endoscope insertion shaft of the plurality of endoscope insertion shafts.

14. The endoscope of claim 13, wherein:

the handle has a rotation collar with a surface designed to assist the surgeon in rotating the endoscope insertion shaft of the plurality of endoscope insertion shafts relative to the handle in a roll dimension about a central axis of the endoscope insertion shaft of the plurality of endoscope insertion shafts.

15. The endoscope of claim 13, wherein:

the electronics inside the handle are designed to sense roll of the endoscope insertion shaft of the plurality of endoscope insertion shafts, and to provide an angular rotation signal designed to permit righting of a displayed image received from the imaging sensor.

16. The endoscope of claim 10, wherein:

the endoscope shafts of the plurality are respectively specialized to surgery on different parts of the body.

17. The endoscope of claim 10, wherein:

the endoscope shafts of the plurality have, respectively, differently-configured imaging sensors at their respective tips.

18. The endoscope of claim 10, wherein:

the endoscope shafts of the plurality have, respectively, imaging sensors at their respective tips mounted at differing field of view angles.

19. The endoscope of claim 10, further comprising:

two or more endoscope insertion shafts of the plurality of endoscope insertion shafts having, respectively, dimensions different than the others, each connectable to the handle at the separation joint, to permit use of the handle in surgery with different requirements for the endoscope insertion shaft.

* * * * *